US010111896B2

(12) United States Patent
Cruz-Moura et al.

(10) Patent No.: US 10,111,896 B2
(45) Date of Patent: Oct. 30, 2018

(54) COMPOSITION COMPRISING A COMBINATION OF DNA METHYLATION INHIBITOR AND A VITAMIN D RECEPTOR AGONIST FOR THE TREATMENT OF DRUG RESISTANT CANCER OR FOR THE PREVENTION OF TUMOR RELAPSE

(71) Applicants: INSERM (Institut National de la Sante et de la Recherche Medicale), Paris (FR); Centre National de la Recherche Scientifique (CNRS), Paris (FR); Universite Paris Descartes, Paris (FR); Fondation Imagine, Paris (FR); Universite Paris Diderot—Paris 7, Paris (FR); Universite Paris-Sud, Orsay (FR); Assistance Publique-Hopitaux de Paris (APHP), Paris (FR)

(72) Inventors: Ivan Cruz-Moura, Paris (FR); Olivier Hermine, Paris (FR); Etienne Paubelle, Paris (FR); Michael Dussiot, Paris (FR); Thiago Trovati Maciel, Paris (FR); Florence Zylbersztejn, Paris (FR)

(73) Assignees: Institut National de la Sante et de la Recherche Medicale (INSERM), Paris (FR); Centre National de la Recherche Scientifique (C.N.R.S.), Paris (FR); Universite Paris Descartes, Paris (FR); Foundation Imagine, Paris (FR); Universite Paris Diderot—Paris 7, Paris (FR); Universite Paris—Sud, Orsay (FR); Assistance Publique-Hopitaux de Paris (APHP), Paris (FR)

( * ) Notice: Subject to any disclaimer, the term of this patent is extended or adjusted under 35 U.S.C. 154(b) by 0 days.

(21) Appl. No.: 15/320,089

(22) PCT Filed: Jun. 19, 2015

(86) PCT No.: PCT/EP2015/063829
§ 371 (c)(1),
(2) Date: Dec. 19, 2016

(87) PCT Pub. No.: WO2015/193480
PCT Pub. Date: Dec. 23, 2015

(65) Prior Publication Data
US 2017/0119804 A1    May 4, 2017

(30) Foreign Application Priority Data
Jun. 19, 2014    (EP) .................................. 14305944

(51) Int. Cl.
*A01N 43/04* (2006.01)
*A61K 31/70* (2006.01)
*A61K 31/706* (2006.01)
*A61K 45/06* (2006.01)
*A61K 31/341* (2006.01)
*A61K 31/53* (2006.01)
*A61K 31/593* (2006.01)

(52) U.S. Cl.
CPC .......... *A61K 31/706* (2013.01); *A61K 31/341* (2013.01); *A61K 31/53* (2013.01); *A61K 31/593* (2013.01); *A61K 45/06* (2013.01)

(58) Field of Classification Search
None
See application file for complete search history.

(56) References Cited

U.S. PATENT DOCUMENTS

| 8,481,514 B2 | 7/2013 | Delansorne et al. |
| 2007/0027120 A1* | 2/2007 | Whitehouse ........... A61K 31/59 514/167 |

FOREIGN PATENT DOCUMENTS

| WO | WO-2010145903 A1 * | 12/2010 | ........... A61K 31/593 |

OTHER PUBLICATIONS

Niitsu et al. British Journal of Haematology (2001), vol. 112, pp. 315-326.*
Gocek et al. Cancers (2011), vol. 3, pp. 2403-2420.*
Dore et al.: "Effect of 5-aza-2'-deoxycytidine and vitamin D3 analogs on growth and differentiation of human myeloid leukemic cells"; Cancer Chemotherapy and Pharmacology, vol. 41, No. 4, 1998, pp. 275-280.
Pan et al.; "Vitamin D stimulates apoptosis in gastric cancer cells in synergy with trichostatin A/sodium butyrate-induced and 5-aza-2'-deoxycytidine-induced PTEN upregulation"; FEBS Journal, vol. 277, No. 4, Feb. 2010, pp. 989-999.
Marik et al.; "DNA methylation-related vitamin D receptor insensitivity in breast cancer"; Cancer Biology & Therapy, vol. 10, No. 1, Jul. 1, 2010, pp. 44-53.
Koschmieder et al.; "Decitabine and Vitamin D3 differentially affect hematopoietic transcription factors to induce monocytic differentiation"; International Journal of Oncology, vol. 30, No. 2, Feb. 2007, pp. 349-355.
Essa et al.; "Signature of VDR miRNAs and Epigenetic Modulation of Vitamin D Signaling in Melanoma Cell Lines"; Anticancer Research, vol. 32, No. 1, Jan. 1, 2012, pp. 383-389.

(Continued)

*Primary Examiner* — Patrick T Lewis
(74) *Attorney, Agent, or Firm* — W&C IP

(57) ABSTRACT

The present invention concerns a combination of (i) a DNA methylation inhibitor, and (ii) a Vitamin D receptor agonist, for simultaneous or sequential use in the treatment of a drug resistant cancer and/or in prevention of tumor relapse in a patient suffering from cancer. The present invention also relates to a combination of (i) a DNA methylation inhibitor, and (ii) a Vitamin D receptor agonist, for increasing, restoring or enhancing sensitivity of a patient suffering from cancer to a chemotherapeutic drug in a patient suffering from cancer.

4 Claims, 23 Drawing Sheets

(56) References Cited

OTHER PUBLICATIONS

Karlic et al.; "Vitamin D supports the efficiency of decitabine for induction of differentiation, apoptosis and osteocalcin expression in leukimia and mastocytosis"; Bone, vol. 51, No. 6, Dec. 2012, p. 512.
Paubelle et al.; "Association of Deferasirox and Vitamin D promotes Cell Differentiation and Improves Overall Survival in Acute Myeloid Leukemia (AML) Elderly Patients After Demethylating Agents Failure: A Retrospective Case Control Study"; Blood: 54th ASH Annual Meeting and Exposition, vol. 120, No. 21, Nov. 16, 2012.

* cited by examiner

Figure 1:
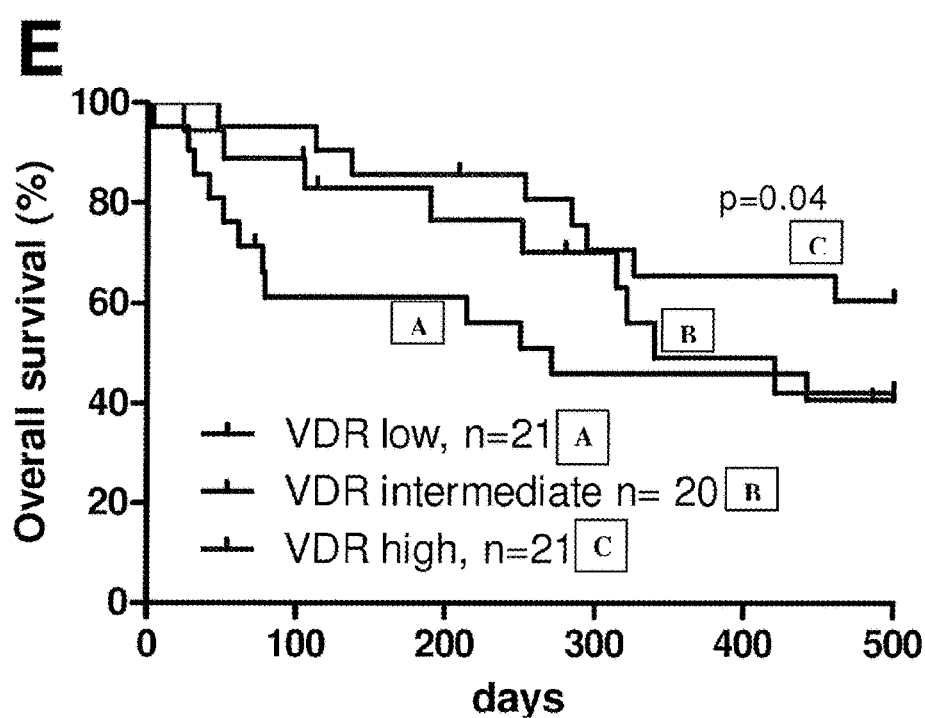

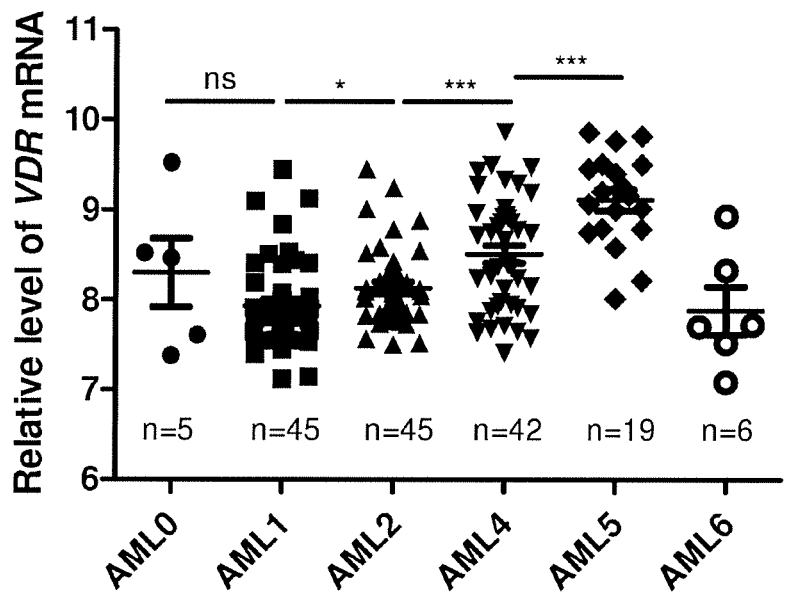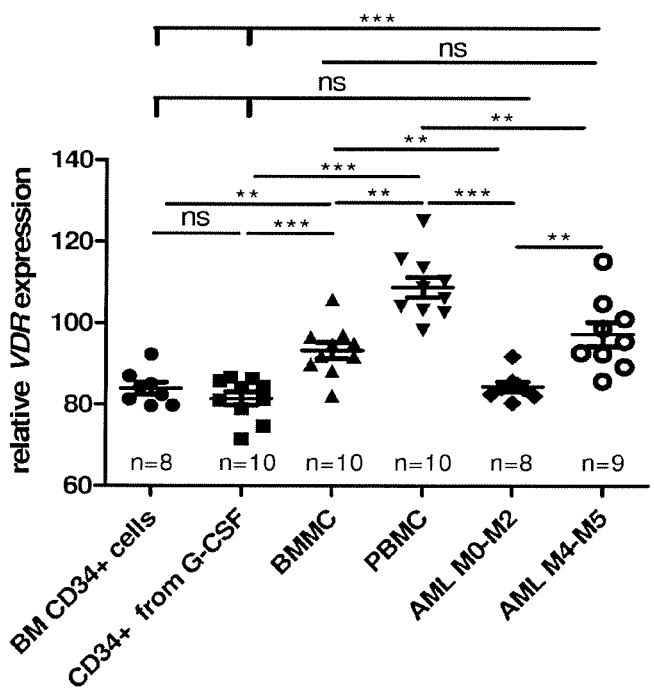
Figure 1 A and B

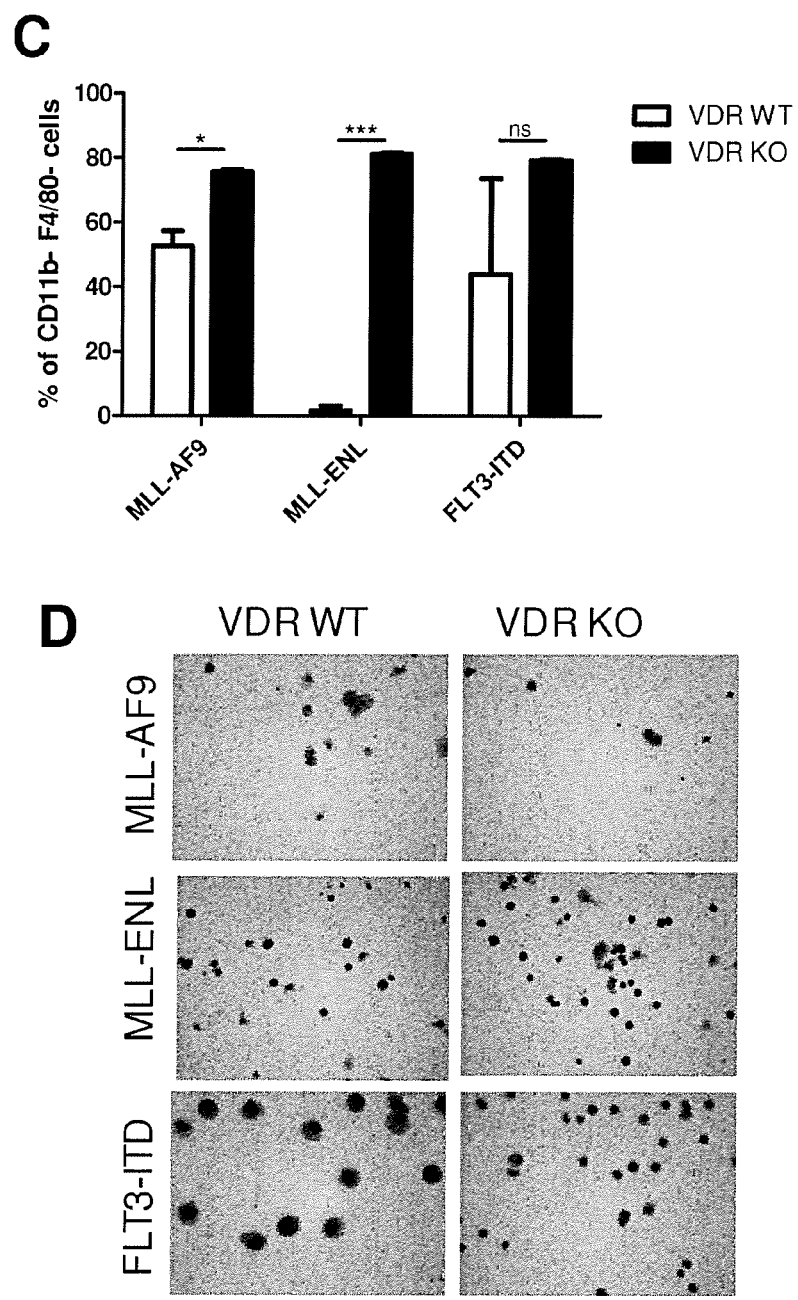
Figure 1 C and D

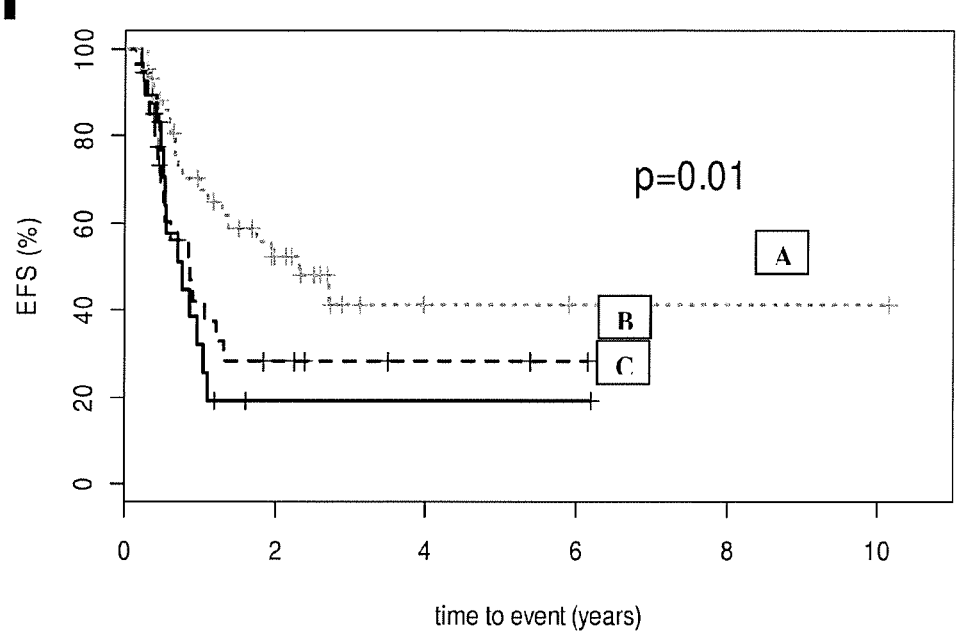
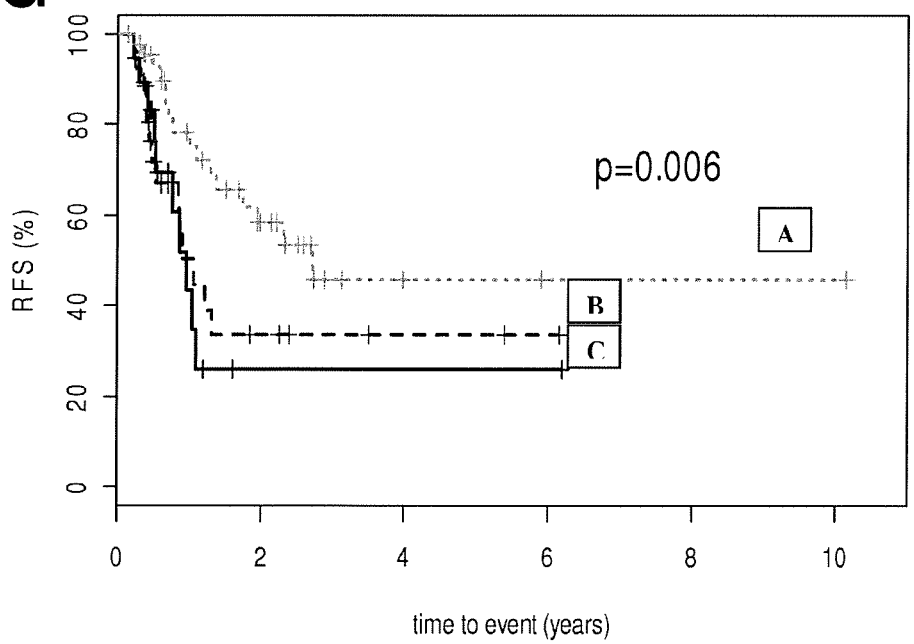
Figure 1 F and G

Figure 2:
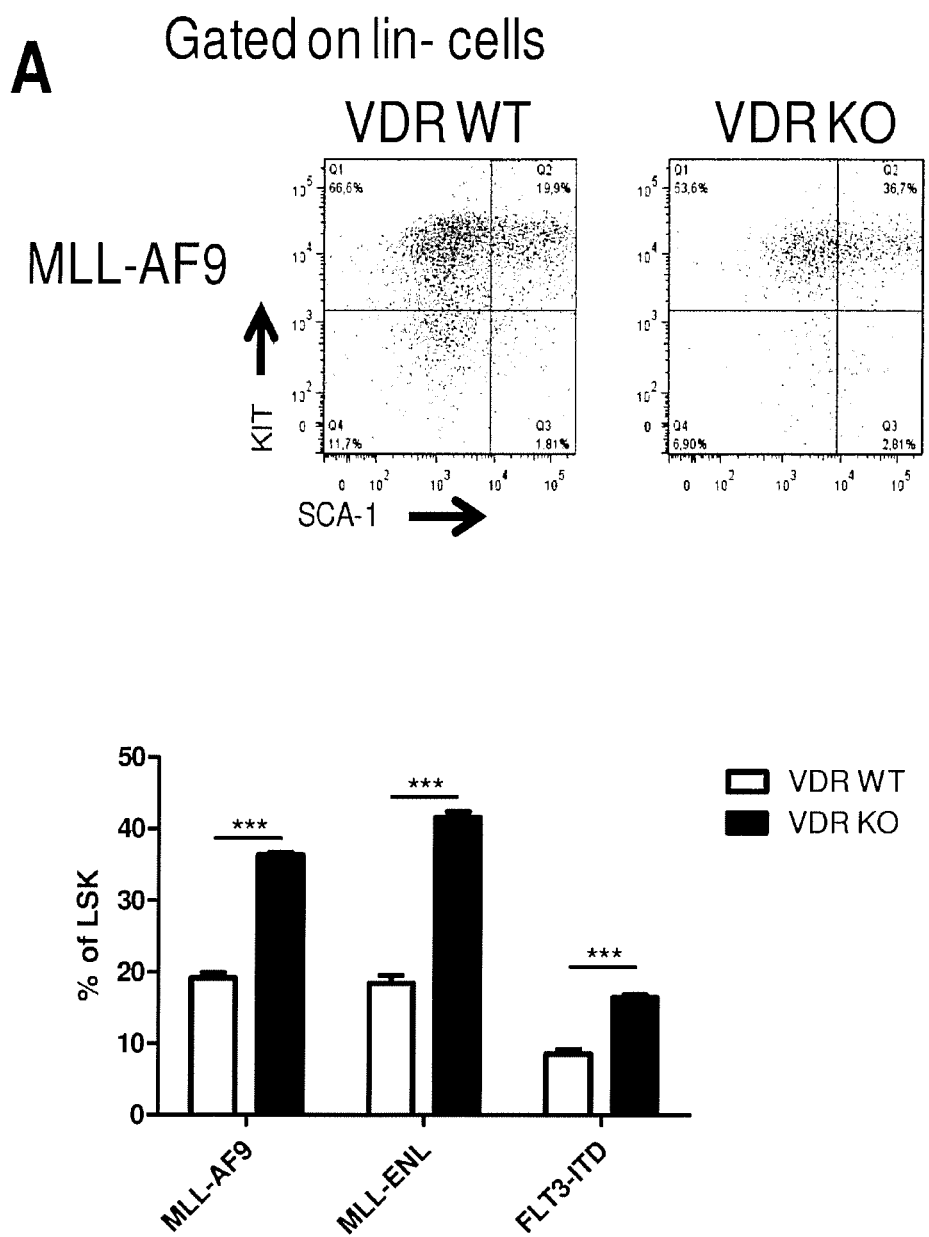
Figure 2:
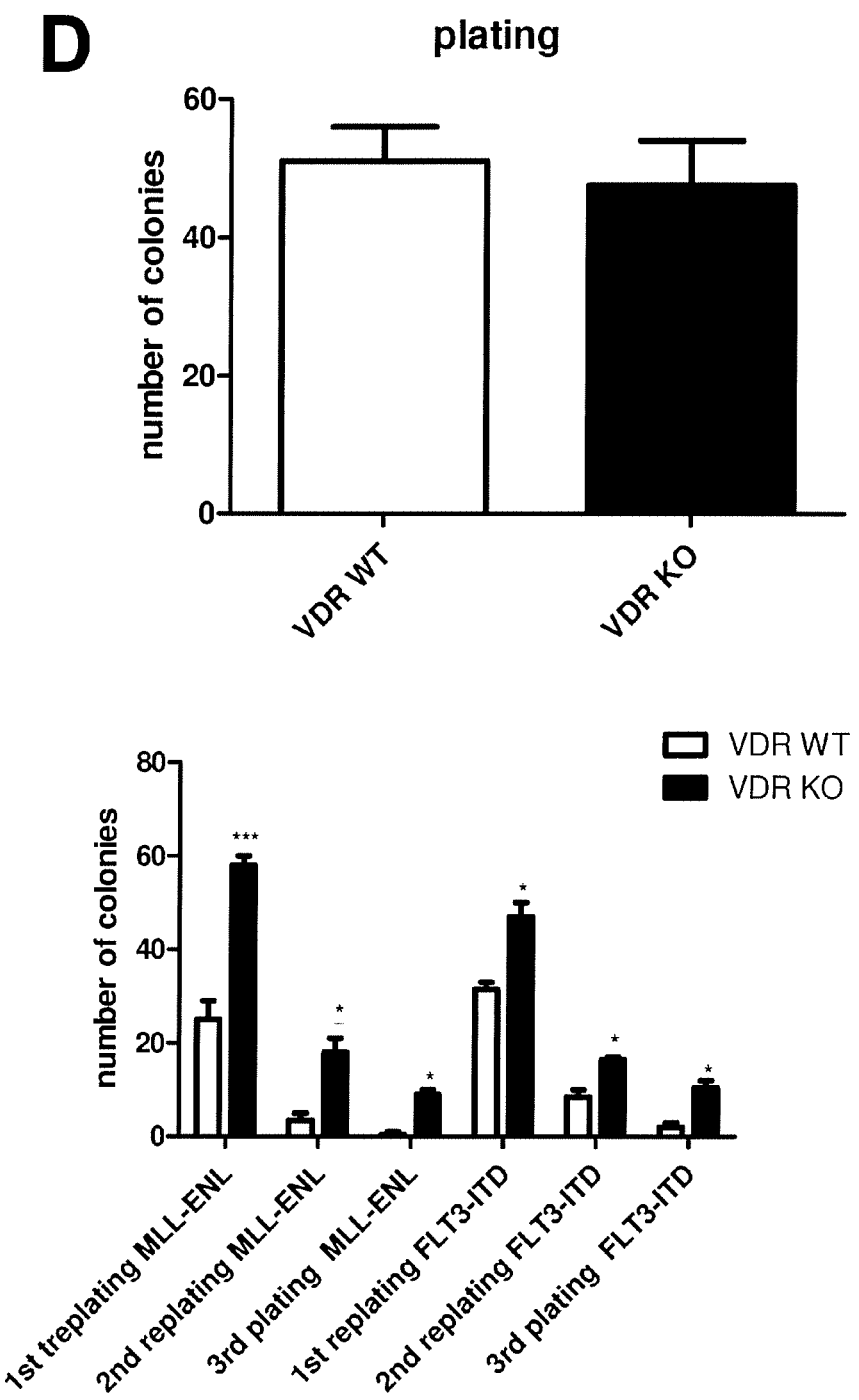

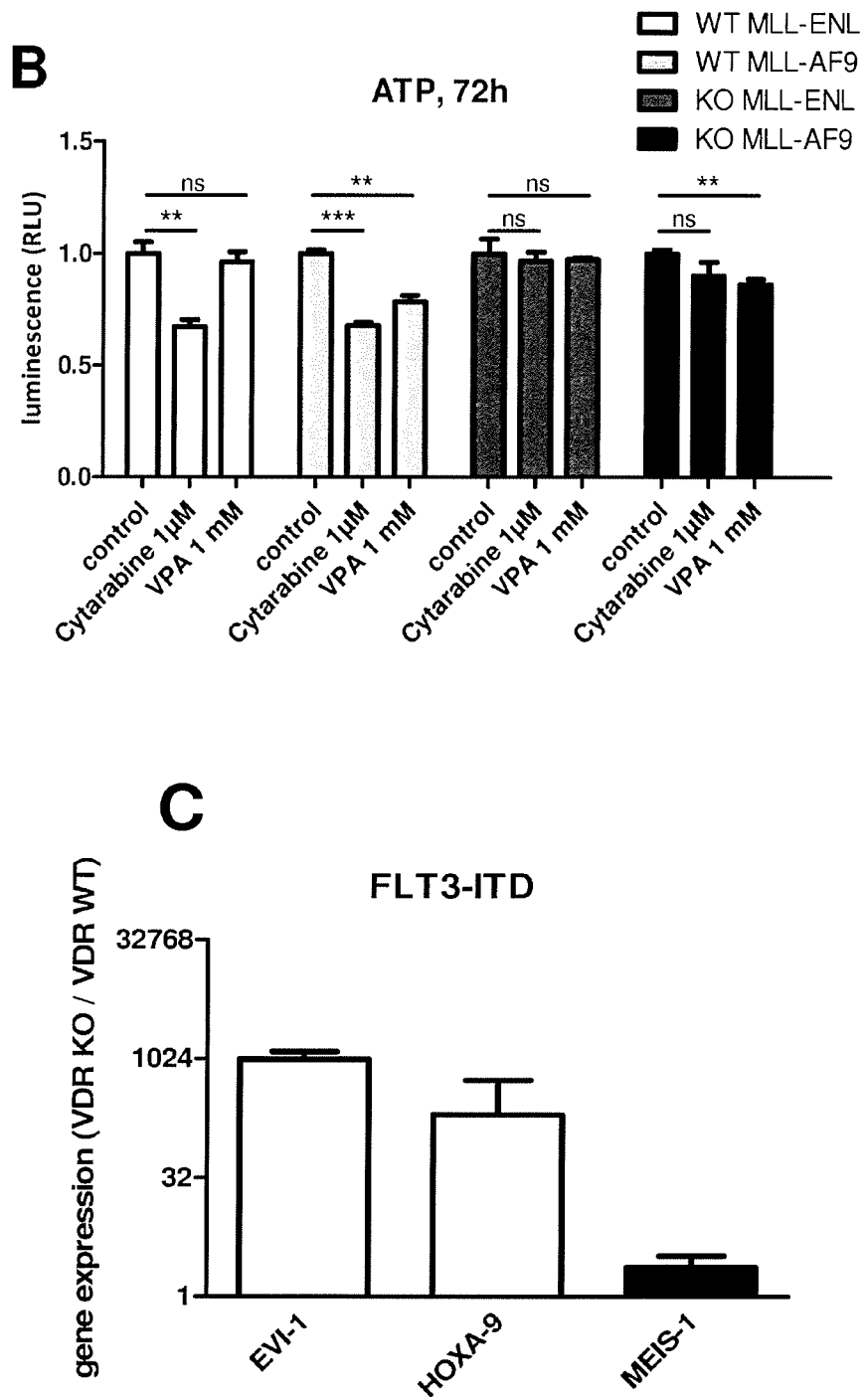
Figure 2 B and C

Figure 3:
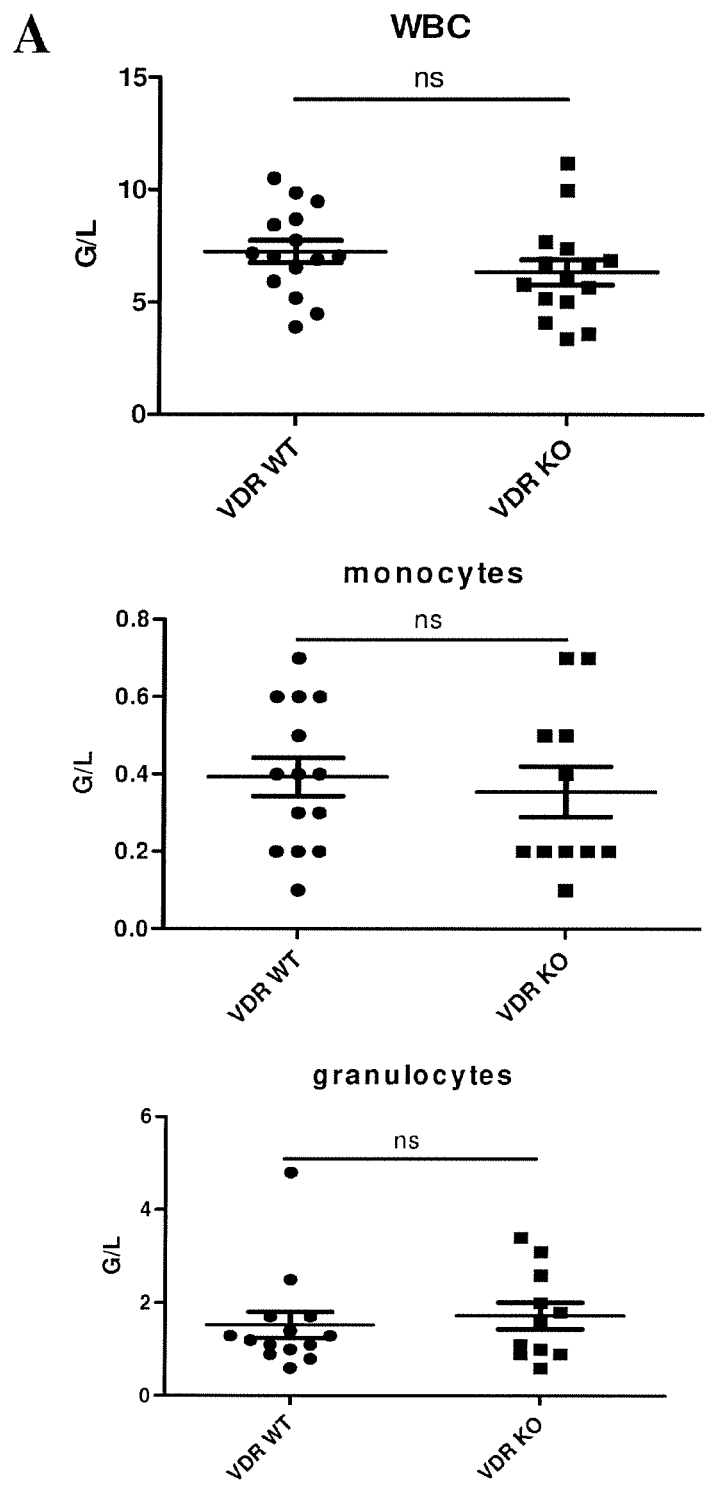
Figure 3:
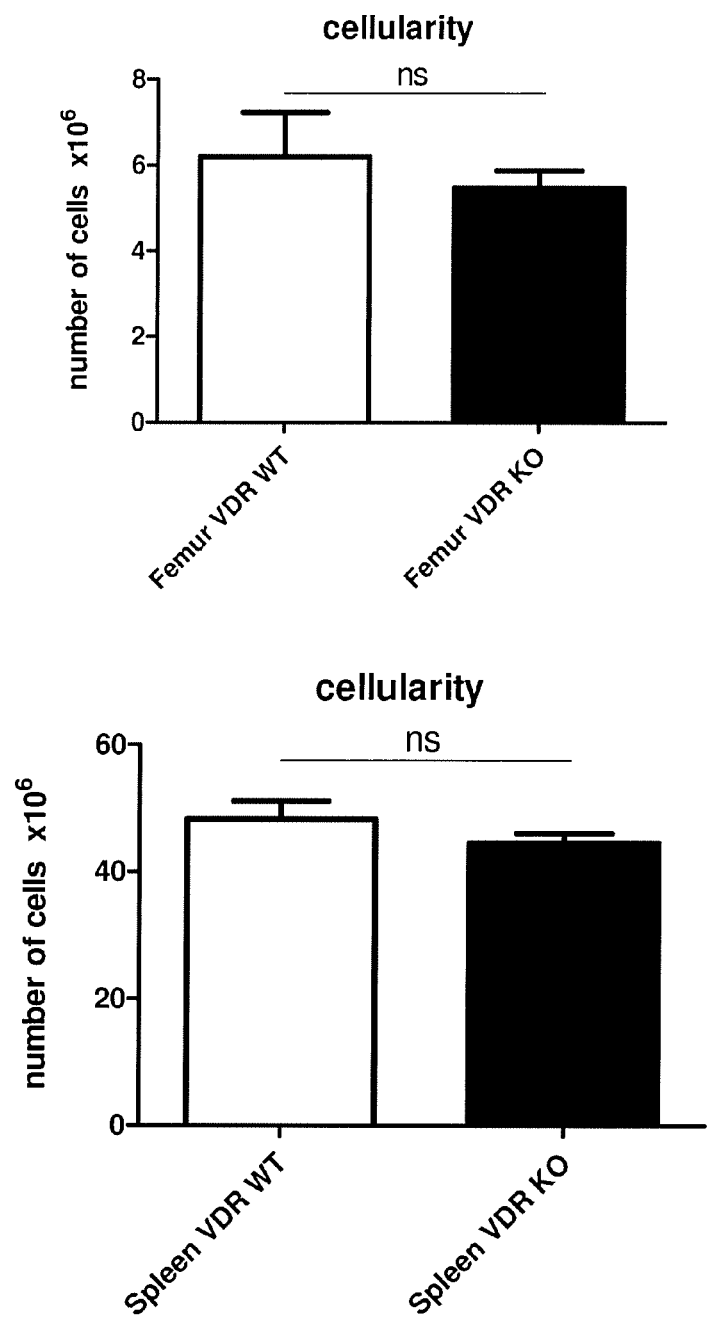
Figure 3:
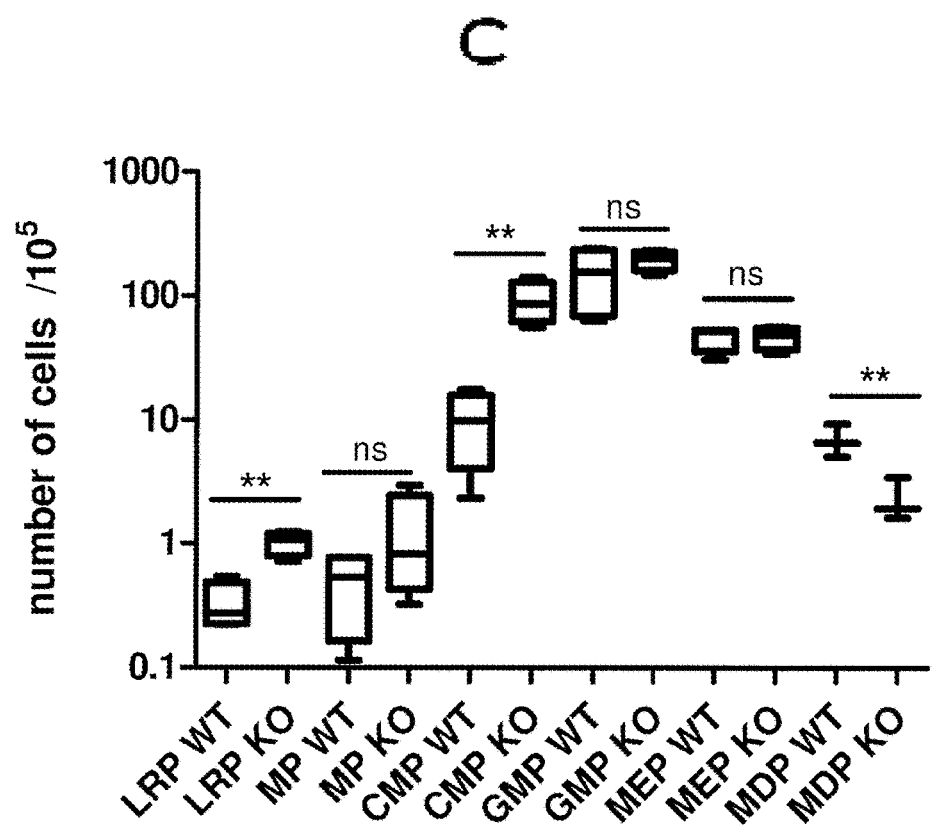
Figure 3:
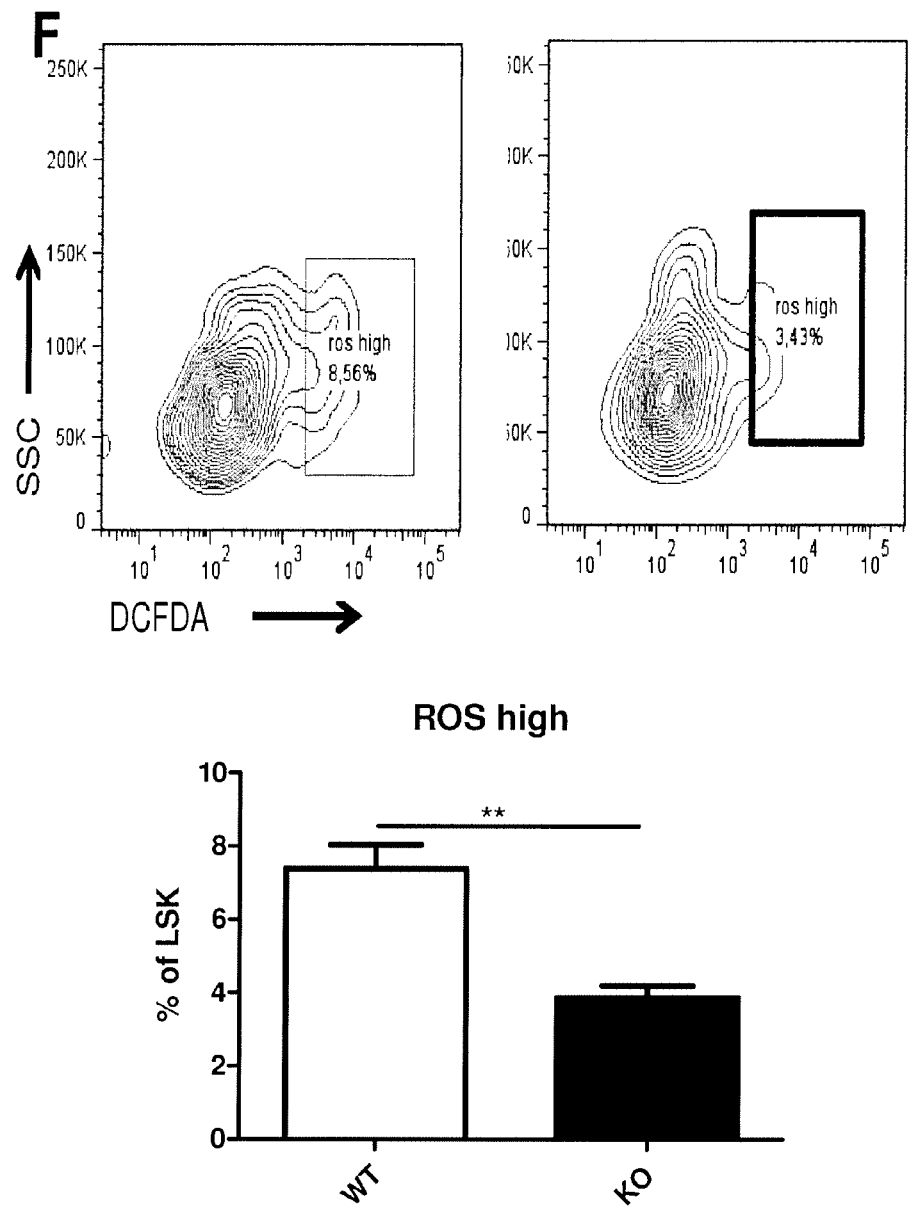
Figure 3:
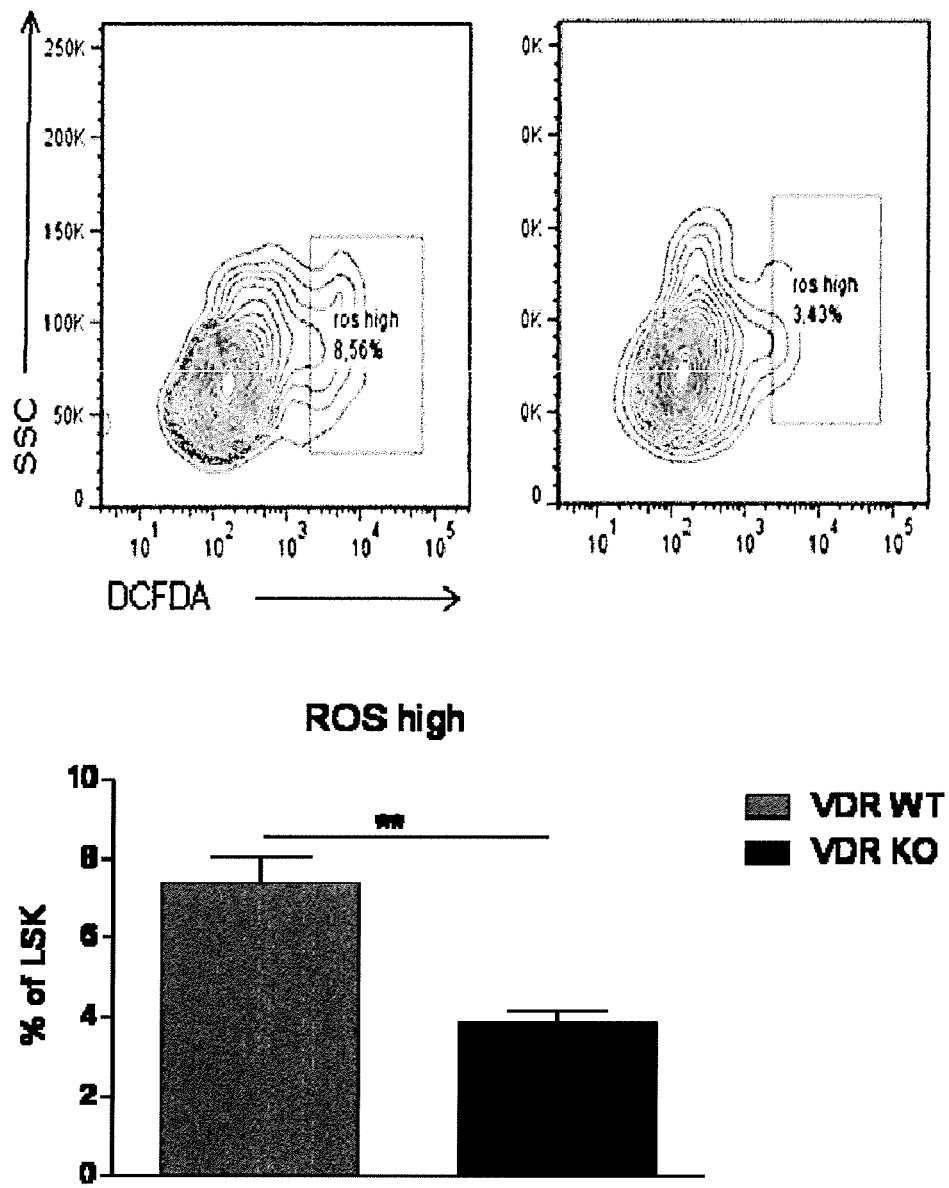

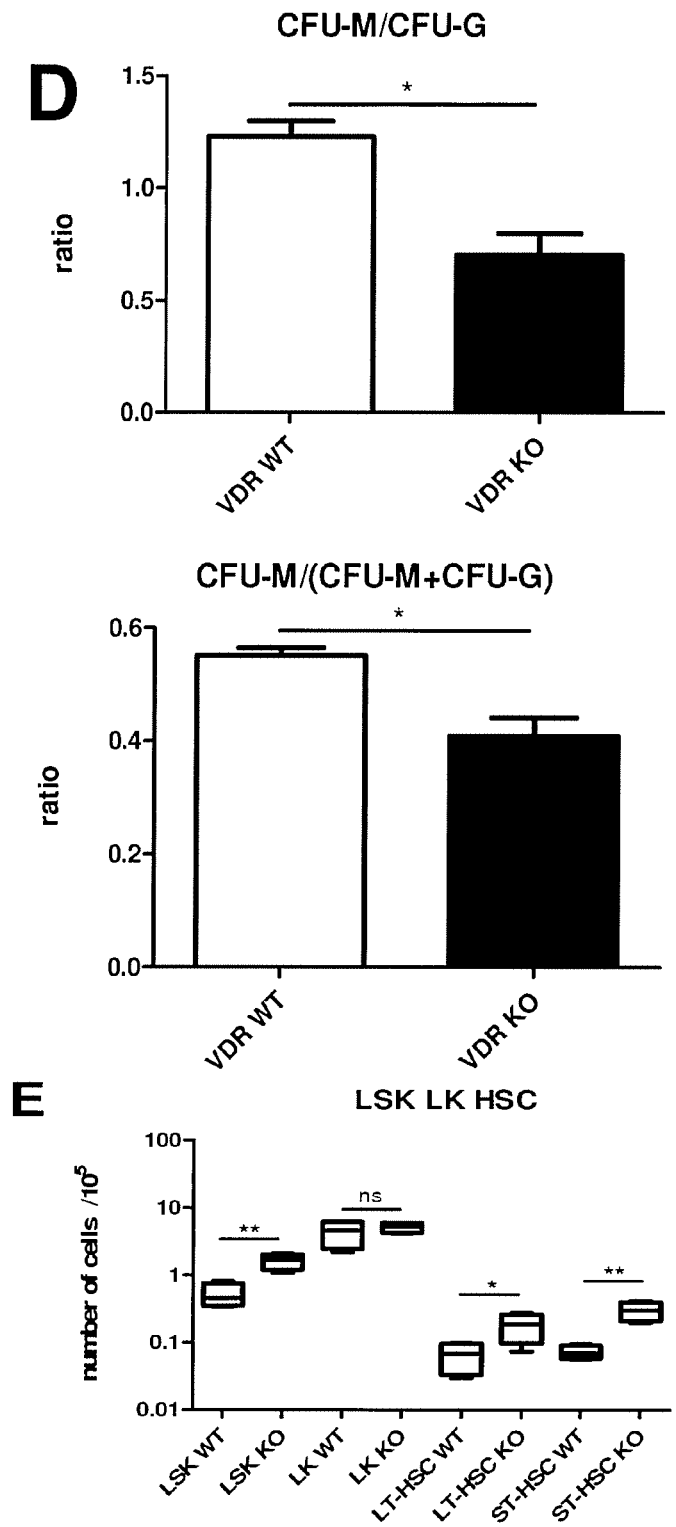
Figure 3 D and E

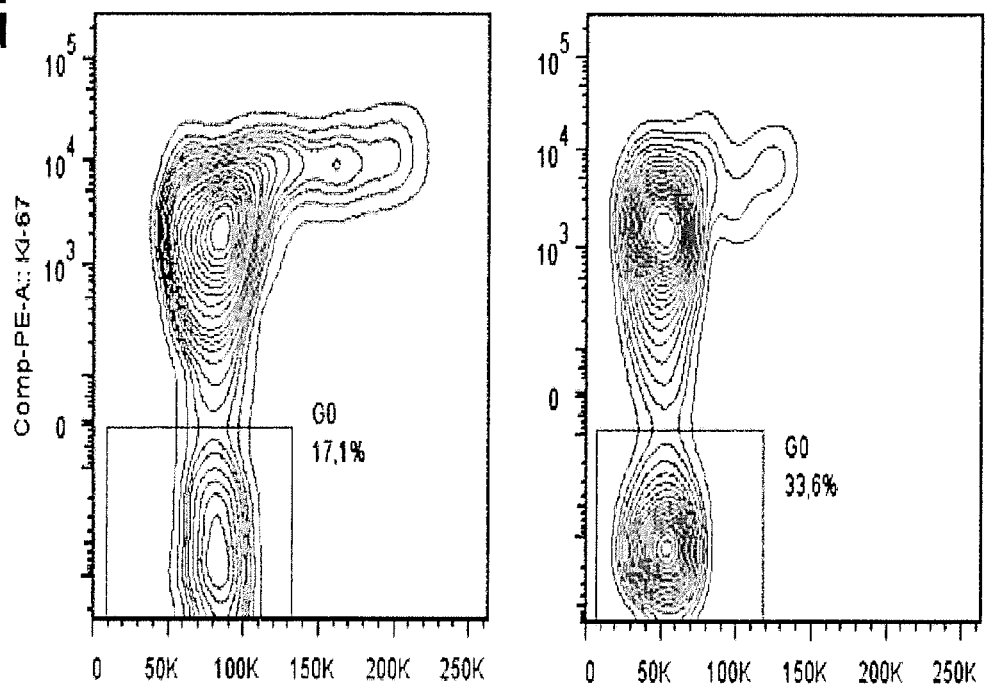
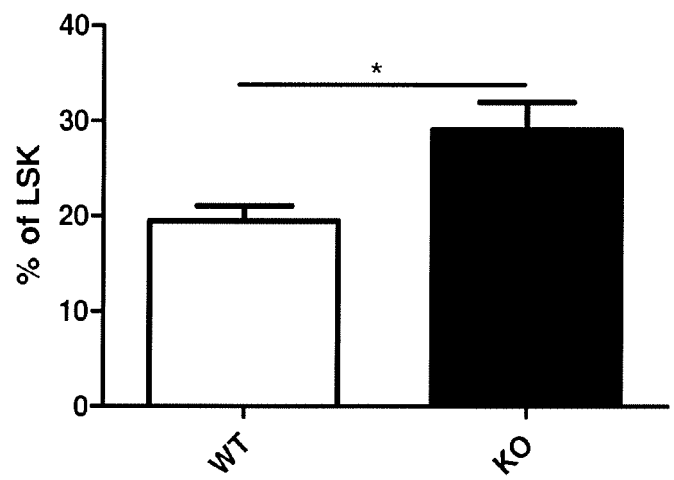
Figure 3 G

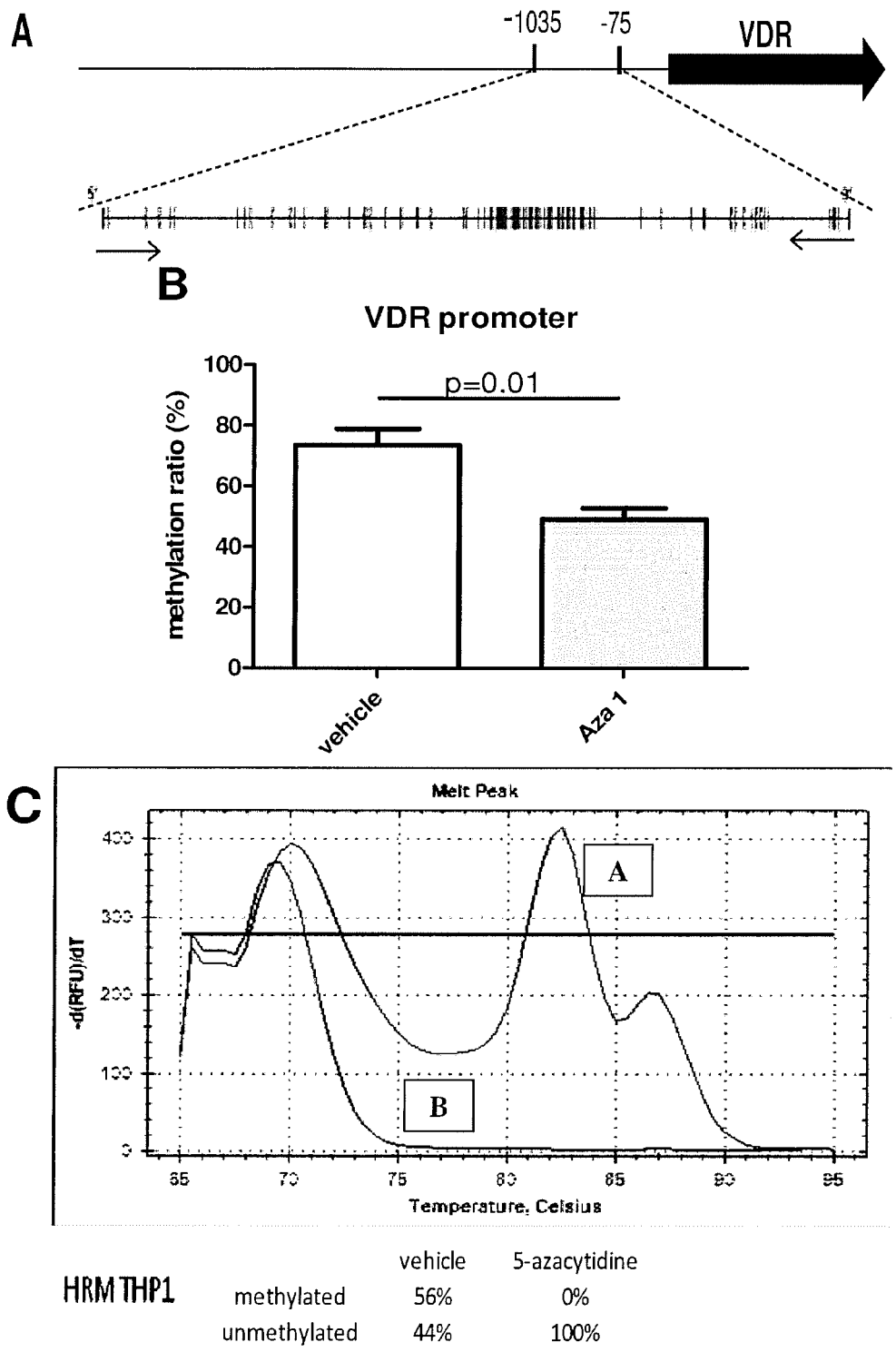
Figure 4 A, B and C

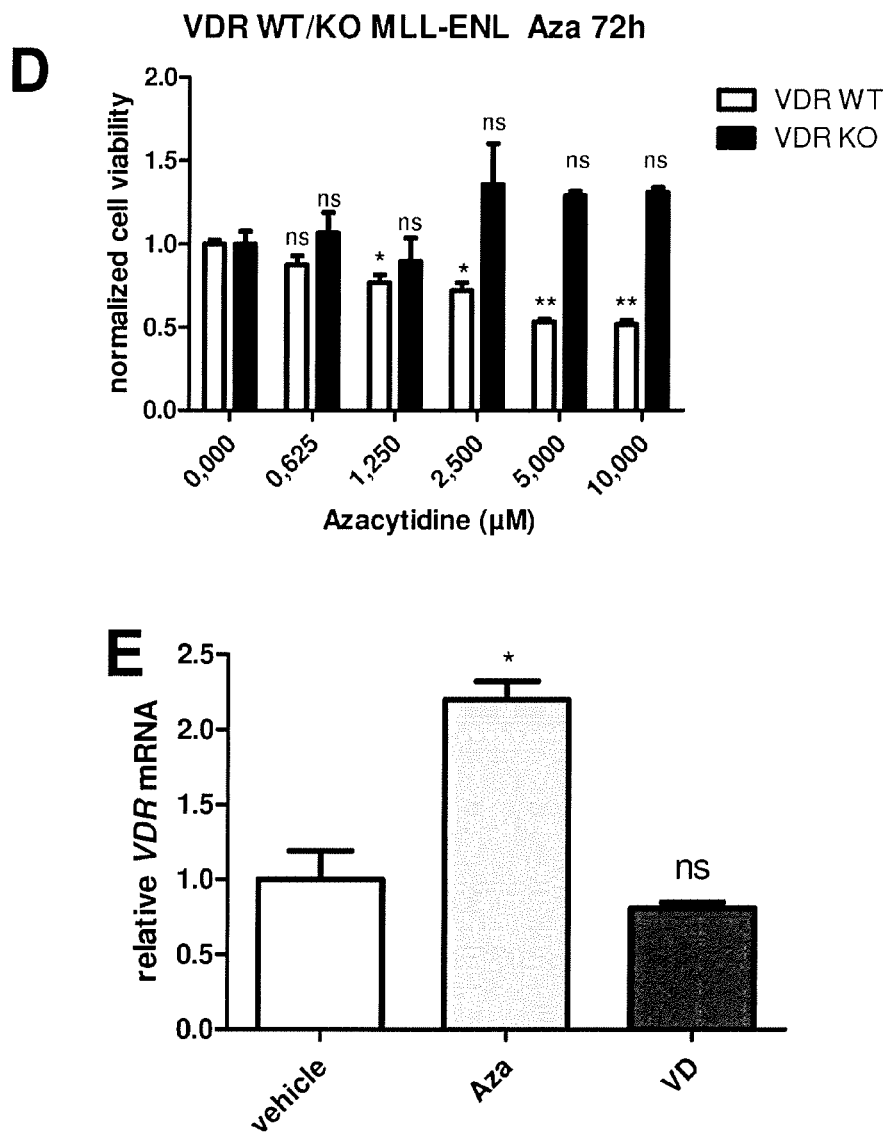
Figure 4 D and E

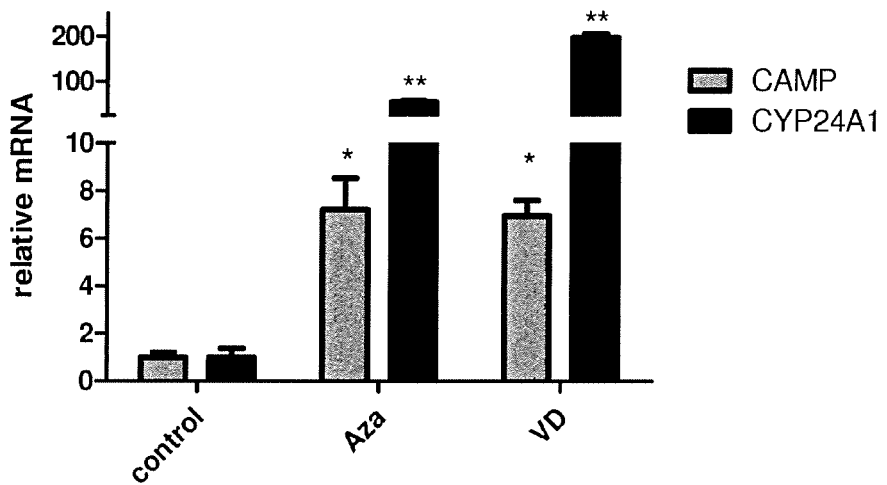
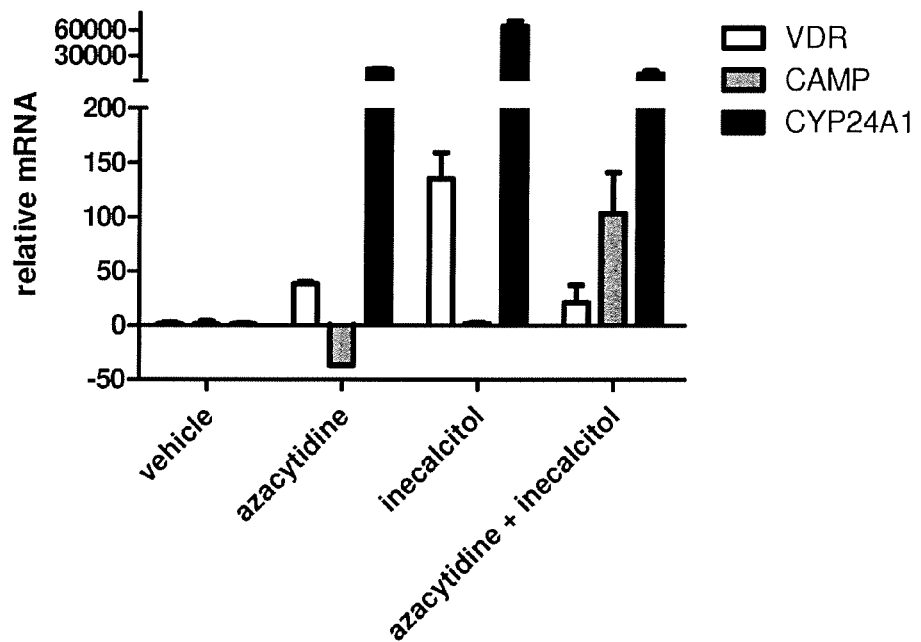
Figure 4 F and G

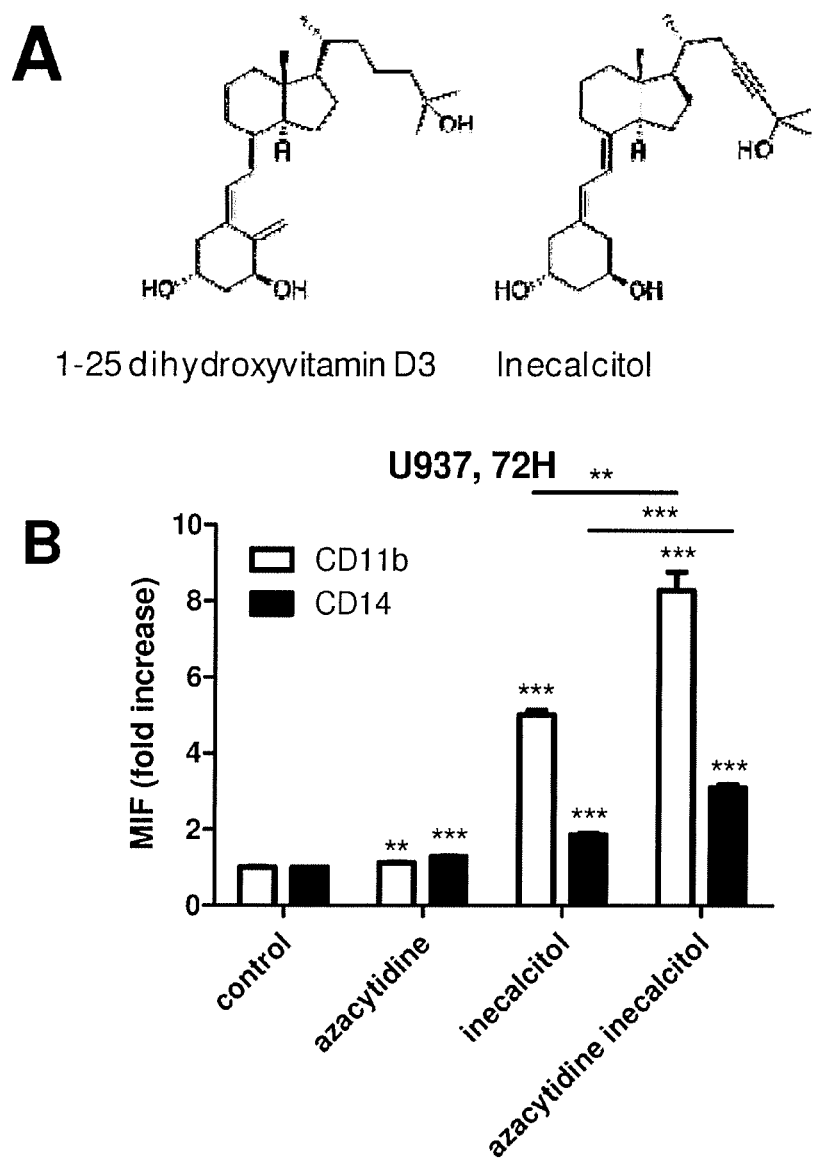
Figure 5 A and B

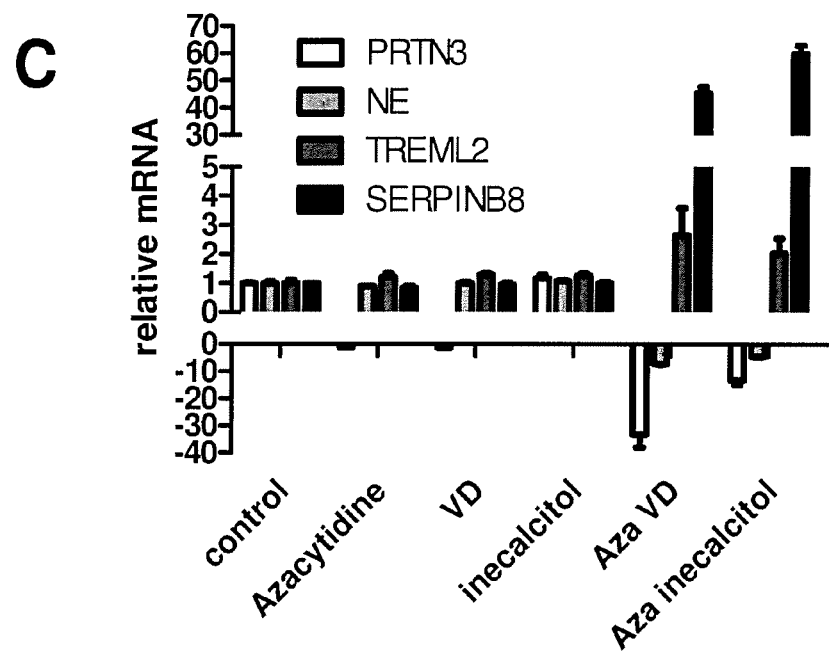
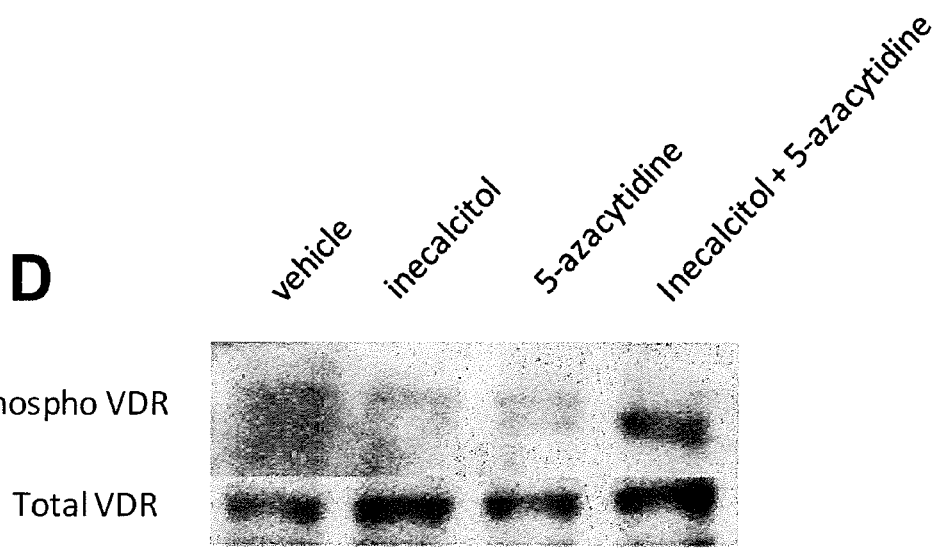
Figure 5 C and D

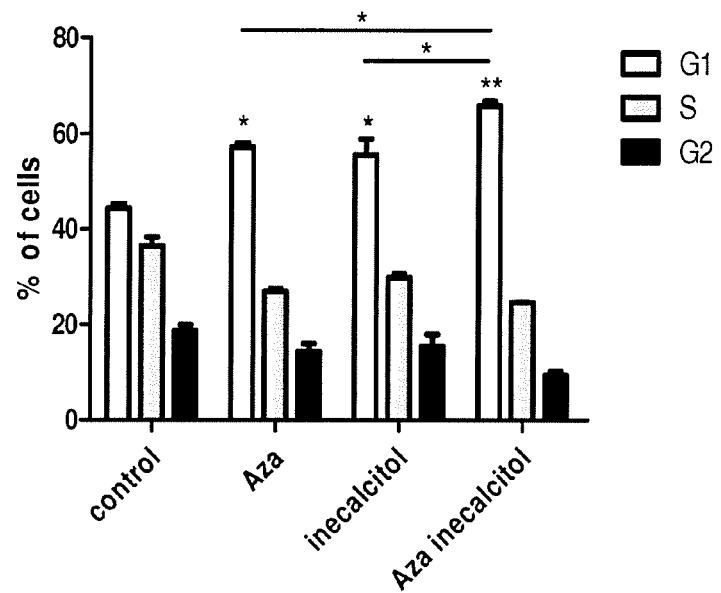
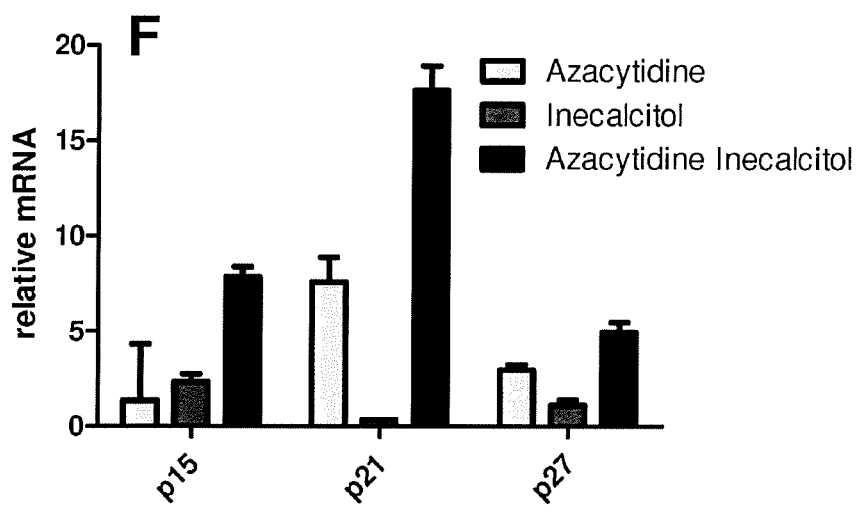
Figure 5 E and F

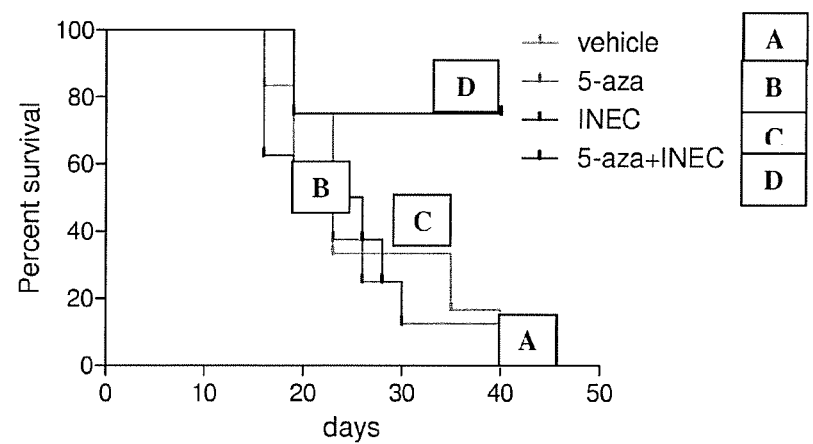
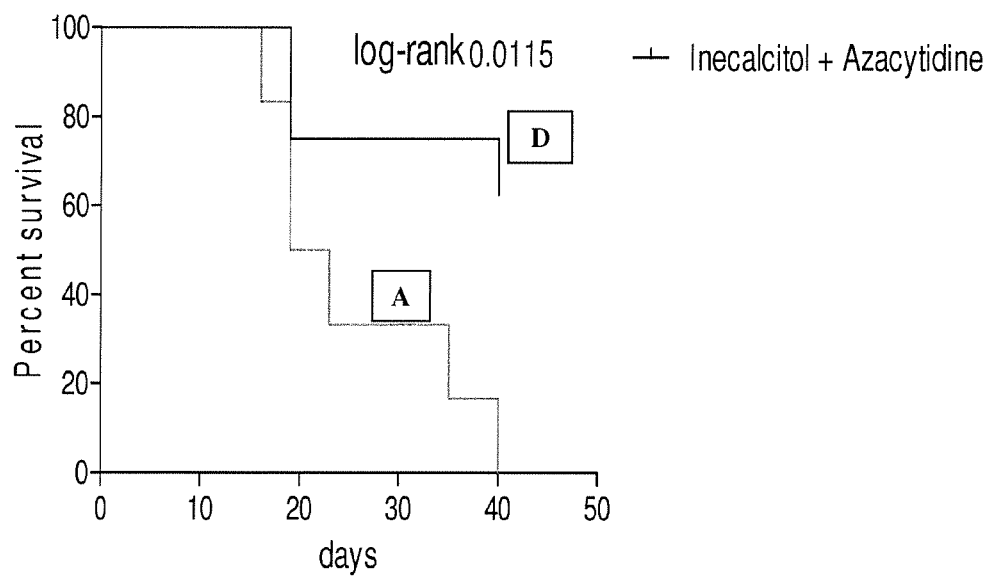
Figure 5 G

COMPOSITION COMPRISING A COMBINATION OF DNA METHYLATION INHIBITOR AND A VITAMIN D RECEPTOR AGONIST FOR THE TREATMENT OF DRUG RESISTANT CANCER OR FOR THE PREVENTION OF TUMOR RELAPSE

FIELD OF THE INVENTION

The present invention concerns a combination of (i) a DNA methylation inhibitor, and (ii) a Vitamin D receptor agonist, for simultaneous or sequential use in the treatment of a drug resistant cancer and/or in prevention of tumor relapse in a patient suffering from cancer. The present invention also relates to a combination of (i) a DNA methylation inhibitor, and (ii) a Vitamin D receptor agonist, for increasing, restoring or enhancing sensitivity of a patient suffering from cancer to a chemotherapeutic drug in a patient suffering from cancer.

BACKGROUND OF THE INVENTION

Acute myeloid leukemia (AML) is a heterogeneous disorder of poor prognosis and is the most frequent form of acute leukemia diagnosed in adults. AML is a clonal malignancy characterized by the accumulation of somatically acquired genetic alterations in hematopoietic progenitor cells (Patel et al., 2012). Recurrent mutations in normal karyotype AML (which comprises nearly 50% of patients) involves a few set of around 30 genes the most recurrent being those affecting FLT3, NPM1, KIT, CEBPA and MLL (Patel et al, 2012; Welch et al, 2012). These mutations intervene in different cellular mechanisms such as self-renewal potential, cell survival/proliferation and myeloid differentiation which ultimately lead to the accumulation of undifferentiated blasts along with impaired normal hematopoiesis (Ferrara and Schiffer, 2013; Lowenberg et al., 1999; Mardis et al., 2009).

Despite chemotherapy and allogenic stem-cell transplantation regimens, AML management remains a challenge since although the bulk of leukemic cells is usually sensitive to chemotherapy, relapses occur and conduct to death. AML resurgence results from the inefficacy of chemotherapy to effectively target quiescent leukemia-initiating cells (LIC) which are able to self-renew and propagate the disease (Bonnet and Dick, 1997; Terpstra et al., 1996). Therefore, therapies aiming to restore LIC sensitivity to chemotherapy would be able to eradicate the disease.

Recently genetic studies have shown that epigenic modifications were associated with disease pathogenesis (Akalin et al., 2012; Figueroa et al., 2010) therefore providing guidance for patients treatment. Even tough, there is still a need to understand molecular mechanisms resulting from epigenetic modifications in AML (Abdel-Wahab and Levine, 2013) and this could help to better identify patients' groups for targeted therapies.

In myelodysplastic syndromes (MDS), DNA methylation has been shown to predict response to therapy (Shen et al., 2010). Furthermore, DNA methyltransferase inhibitors such as 5-azacytidine (5-AZA) or decitabine have shown to increase time to transformation of MDS in AML (Fenaux et al., 2010). However, response rates were time-limited and the molecular mechanism involved in the efficacy of DNA methyltransferase inhibitors is unknown (Garcia-Manero and Fenaux, 2011). Therefore, the identification of these molecular pathways could assist to determine new therapeutic associations able to increase the efficacy of DNA methyltransferase inhibitors.

Inventors have previously shown that iron deprivation therapy promotes monocytic differentiation of AML cells through the induction of reactive oxygen species (ROS) (Callens et al., 2010a). An analysis of gene expression patterns revealed that 30% of the most significant genes induced by iron homeostasis-targeting therapy presented a vitamin D receptor (VDR) signaling signature. Iron chelating agents acted synergistically with VD through the induction of VDR signaling and activation of downstream MAPKs pathway. Recently, inventors have shown in a retrospective study that combined iron chelators and vitamin D therapy is associated with increased overall survival in a retrospective cohort of elderly patients (Paubelle et al., 2013). Therefore, induction of VDR expression/activity is a potential therapeutic target in AML.

Inventors further investigated the correlation existing between VDR expression/activity and the molecular mechanisms involved in AML pathology and showed that VDR expression is downregulated in AML by an epigenic mechanism and that this was correlated with patient prognosis. Impaired VDR expression/activity limited tumor blast cells differentiation and increased stemness in both normal and malignant models. Combined treatment of AML cells with DNA-demethylating agents and VDR agonists blocked tumor propagation in mice, decreased cell stemness and restored LIC sensitivity to chemotherapy. Therefore, inventors propose that VDR expression controls major molecular mechanisms involved in monocyte differentiation, hematopoietic stem cell self-renewing and LIC longevity, which have consequences in AML pathogenesis.

SUMMARY OF THE INVENTION

In a first embodiment, the invention relates to a combination of a) a DNA methylation inhibitor; and b) a Vitamin D receptor agonist, for simultaneous or sequential use in the treatment of drug resistant cancer.

In a second embodiment, the invention relates to a combination of a) a DNA methylation inhibitor; and b) a Vitamin D receptor agonist, for simultaneous or sequential use in the prevention of tumor relapse in a patient suffering from cancer.

In a third embodiment, the invention relates to a combination of a) a DNA methylation inhibitor; and b) a Vitamin D receptor agonist for simultaneous or sequential use in enhancing sensitivity to a chemotherapeutic drug in a patient suffering from cancer.

DETAILED DESCRIPTION OF THE INVENTION

The present invention arises from the unexpected finding by the inventors that DNA methylation inhibitors act synergistically with vitamin D receptor agonists, in particular through the epigenetic modification via VDR promoter demethylation resulting in the lifting of the blockade of VDR expression. This association has proved to be effective in vitro in AML blasts and in vivo in AML xenografted tumors in mice. The inventors have also shown that the combination therapy improves the condition of AML patient refractory to chemotherapy and induced cell differentiation quiescent leukemia-initiating cells (LIC) in a patient.

The inventors also surprisingly uncovered that administration of the combination of the invention sensitized cancer cells, quiescent leukemia-initiating cells (LIC) to chemotherapy. In particular, restoration of expression of VDR may sensitizes cancer cells to lower doses of chemotherapy drugs.

The inventors thus propose a new targeted therapy for treating drug resistant disease and notably, drug resistant cancer. The invention is particularly advantageous for treating cancer expressing VDR. Without being bound to any theory, the inventors believe that re-expressing VDR in drug resistant cells such as drug resistant tumors, in which VDR expression is significantly reduced, allows preventing drug resistance from developing in nonresistant cells, increases or restores sensitivity of drug resistant cells to therapeutic or prophylactic agents, and increases the sensitivity to notably anti-mitotic agents such as taxanes. As a consequence, lower doses of anti-mitotic agents can be administered to the patient, thereby reducing side effects while maintaining efficacy of the anti-mitotic agent.

Combination of a DNA Methylation Inhibitor with a Vitamin D Receptor Agonist, for Use in the Treatment of Drug Resistant Cancer and/or in the Prevention of Tumor Relapse The present invention provides a combination of:
i. a DNA methylation inhibitor; and
ii. a Vitamin D receptor agonist;
for simultaneous or sequential use in the treatment of drug resistant cancer in a patient suffering from cancer.
The present invention also provides a combination of:
i. a DNA methylation inhibitor; and
ii. a Vitamin D receptor agonist,
for simultaneous or sequential use in the prevention of tumor relapse in a patient suffering from cancer.

As defined herein the expression "DNA methylation inhibitor" also called "Demethylating agent", refers to a class of compounds that interfere with DNA methylation which is the addition of a methyl group to the 5-position of the cytosine pyrimidine ring or the nitrogen in position 6 of the adenine purine ring. DNA methylation stably alters the gene expression pattern in cells i.e. decrease gene expression (i.e. for the Vitamin D receptor)

Demethylating agents are compounds that can inhibit methylation, resulting in the expression of the previously hypermethylated silenced genes. Cytidine analogs such as 5-azacytidine (azacitidine) and 5-azadeoxycytidine (decitabine or dacogene) are the most commonly used demethylating agents. These compounds work by binding to the enzymes that catalyse the methylation reaction, i.e. DNA methyltransferases.

Azacitidine and decitabine are preferred DNA methylation inhibitors that can be used within the frame of the present invention. The dose used for azacitidine or decitabine is from 1 to 10 microM, preferably from 2.5 microM to 5 micro M.

In preferred embodiment, the DNA methylation inhibitor is azacytidine.

As defined herein the expression "vitamin D receptor agonist" refers to a compound which is able to activate the vitamin D receptor (VDR), and preferably is able to induce cell differentiation upon binding to the VDR.

Preferably, the "vitamin D receptor agonist" is selected from the group consisting of vitamin D and/or vitamin D analogs and/or vitamin D receptor modulators.

As used herein the term "vitamin D" comprises all the forms of vitamin D or its precursor, as for example vitamin D1, vitamin D2 (ergocalciferol), vitamin D3 (cholecalciferol), vitamin D4 (22-dihydroergocalciferol) and vitamin D5 (sitocalciferol). Preferably, the "vitamin D" according to the invention is vitamin D3, more preferably vitamin D3 in its active form 1α,25-dihydroxycholecalciferol D3 (1,25-(OH) 2D3 or calcitriol).

Preferably, the "vitamin D precursor" according to the invention is the vitamin D3 precursor (i.e calcifediol (vitamin D3 precursor also known as calcidiol, 25-hydroxycholecalciferol)).

As intended herein a "vitamin D analog" or a "vitamin D receptor modulator" are able to bind to the vitamin D receptor (VDR) and preferably are able to induce cell differentiation upon binding to the VDR.

Tests for determining the capacity of a vitamin D analog or of a vitamin D receptor modulator to bind to the vitamin D receptor are well known to the person skilled in the art. Preferably, this capacity can be evaluated by estimating the specific binding of the analog or of the vitamin D receptor modulator on a cell extract. For example, in a typical binding experiment, soluble cell extract obtained by sonication is incubated with increasing concentration of vitamin D analog or of vitamin D receptor modulator. Bounds and free analogs can be separated by the hydroxylapatite method. Specific binding may be calculated by subtracting non-specific binding obtained in the presence of an excess 1,25-(OH)2D3 from the total binding measured in absence of 1,25-(OH) 2D3 (Skowronski et al. (1995) Endocrynology 136(1): 20-26).

The capacity of the analog or of vitamin D receptor modulator to induce cell differentiation can be measured by various methods well known to the person skilled in the art. For example, this capacity can be estimated by the measure of the induction of monocyte differentiation or CD11b/CD14 expression (a marker of cellular differentiation) in a LNCaP cell line after incubation with the analog or with the vitamin D receptor modulator as described in Skowronski et al (Skowronski et al. (1995) Endocrynology 136(1): 20-26) .).

Many vitamin D analogs are well known in the art. The expression "vitamin D analog" notably encompasses vitamin D metabolites, vitamin D derivatives and vitamin D precursors, preferably it encompasses vitamin D3 metabolites, vitamin D3 derivatives and vitamin D3 precursors.

Vitamin D analogues according to the invention can retain the secosteroid structure with modified side chain structures around the C-24 position. For example, the vitamin D analog may be paricalcitol (19-nor-1α(OH)2D2), ILX23-7553 (16-ene-23-yne-1α,25(OH)2D3), OCT (Maxacalcitol, 22-oxa-1α,25(OH)2D3) and EB1089 (Seocalcitol, 1α-dihydroxy-22,24-diene-24,26,27-trihomo-vitamin D3).

More preferably, the vitamin D analog according to the invention is selected from the group consisting paricalcitol, OCT, EB1089, 14-epi-analog of $1,25D_3$ and inecalcitol [19-nor-14-epi-23-yne-1,25-$(OH)_2D_3$; TX522].

In a particular embodiment, the "vitamin D analog" according to the invention is inecalcitol [19-nor-14-epi-23-yne-1,25-$(OH)_2D_3$; TX522].

Vitamin D receptor modulators (VDRMs) according to the invention are preferably non-secosteroidal compounds (mostly chemical entities) that have been shown to be less hypercalcemic than the VD analogues, as for example the compounds mentioned in US 2008/0200552, WO2005051936, WO2005051938, WO2005051893, and WO2006069154. More preferably, the vitamin D receptor modulator (VDRMs) is selected from the group consisting of LY2108491, LY2109866 and LG190119 (Ma et al. (2006) J Clin Invest 116(4):892-904, Polek et al (2001) Prostate 49(3):224-33).

In a most preferred embodiment, the Vitamin D receptor agonist is Vitamin D3 or inecalcitol.

In the context of the invention, the term "treatment or prevention" means reversing, alleviating, inhibiting the progress of, or preventing the disorder or condition to which such term applies, or one or more symptoms of such disorder or condition. In particular, the treatment of the disorder may consist in reducing the number of malignant cells. Most preferably, such treatment leads to the complete depletion of the malignant cells.

Preferably, the individual to be treated is a human or non-human mammal (such as a rodent (mouse, rat), a feline, a canine, or a primate) affected or likely to be affected with cancer. Preferably, the individual is a human.

"Drug resistance" as used in expressions such as "drug resistant cancer" or "drug resistant cells" or "drug resistant disease" means a circumstance where a disease (e.g., cancer) does not respond to a therapeutic agent. Drug resistance can be intrinsic, which means that the disease has never been responsive to the therapeutic agent, or acquired, which means that the disease ceases responding to the agent or agents to which the disease had previously been responsive. For cancers, such therapeutic agent may be a chemotherapeutic drug such as colchicine, vinblastine, doxorubicin, vinca alkaloids, etoposide, taxanes, or other small molecules used in cancer chemotherapy. Drug resistance may be associated with cancer and other conditions, such as bacterial, viral, protozoal, and fungal diseases.

By "tumor relapse" or "cancer recurrence" is meant the return of cancer after treatment and after a period of time during which the cancer cannot be detected: in a another term it means reappearance of cancer after a disease-free period.

The terms "cancer" "malignancy" and "tumors" refer to or describe the pathological condition in mammals that is typically characterized by unregulated cell growth. More precisely, in the use of the invention, diseases, namely tumors that express vitamin D receptor are most likely to respond to vitamin D modulators. In particular, the cancer may be associated with a solid tumor or unregulated growth of undifferentiated hematopoietic bone marrow cells (hematopoietic stem cell). Examples of cancers that are associated with solid tumor formation include breast cancer, uterine/cervical cancer, oesophageal cancer, pancreatic cancer (Albrechtsson et al Pancreatology 2003), colon cancer, colorectal cancer, kidney cancer, ovarian cancer, prostate cancer, head and neck cancer, non-small cell lung cancer and stomach cancer. Preferably the solid tumor is breast cancer.

Preferably, the cancer or malignancy or tumor according to the invention is due to an unregulated growth of undifferentiated hematopoietic bone marrow cells (hematopoietic stem cell).

As intended herein the expression "hematopoietic stem cell (HSC)" refers to adult multipotent stem cells that give rise to all the blood cell types including for example myeloid lineages (monocytes and macrophages, neutrophils, basophils, eosinophils), erythrocytes, megakaryocytes/platelets, and lymphoid lineages (T-cells, B-cells, NK-cells).

The expression "hematopoietic stem cell malignancy" or "hematopoietic malignancy" according to the invention comprises acute myeloid leukemia (AML), acute lymphoblastic leukemia, Chronic myeloid, lymphoid leukemia, lymphoma and myelodysplastic syndrome (as defined in 2008 WHO classification). Preferably, the hematopoietic malignancy according to the invention is selected from the group consisting of acute myeloid leukemia.

Preferably, the acute myeloid leukemia according to the invention is AML with normal karyotype with mutation in gene selected from the group consisting of: FLT3, NPM1, KIT, CEBPA and MLL (Patel et al, 2012; Welch et al, 2012).

The impact of several mutations has been explored this last decade in AML, the most frequent being the internal tandem duplication (ITD) in the juxta-membrane domain of the Fms-Like Tyrosine kinase 3 (FLT3), which leads to constitutive activation of this receptor (Nakao M et al, Leukemia 1996). This mutation is particularly associated to normal karyotype AML (Thiede C et al, Blood 2002) and now is part to the most recent prognostic classification of AML (Döhner H et al, Blood 2010). During normal myeloid hematopoiesis, FLT3 is highly expressed and reported to play an important role at the granulo-monocyte progenitor level (Böiers C et al, Blood 2010).

More preferably, the acute myeloid leukemia according to the invention is AML which express mutated FLT3-ITD.

The DNA methylation inhibitor can be administered prior to, concomitantly with, or subsequent to the administration of the vitamin D receptor agonist to an individual which had, has, or is susceptible to develop a cancer, more specifically a drug resistant cancer; as defined above. The DNA methylation inhibitor and the vitamin D receptor agonist can be administered to an individual in a sequence and within a time interval such that the first binding molecule can act together with the second binding molecule to provide an increased benefit than if they were administered otherwise. Preferably, the DNA methylation inhibitor and the vitamin D agonist are administered together.

The present invention also provides a combination of:
i. a DNA methylation inhibitor; and
ii. a Vitamin D receptor agonist;
for simultaneous or sequential use in the treatment of drug resistant cancer in a patient suffering from hematopoietic stem cell malignancy, said combination being capable of eradicating quiescent leukemia-initiating cells (LIC).

The present invention also provides a combination of:
iii. a DNA methylation inhibitor; and
iv. a Vitamin D receptor agonist,
for simultaneous or sequential use in the prevention of tumor relapse in a patient suffering from hematopoietic stem cell malignancy said combination being capable of preventing relapse by eradicating quiescent leukemia-initiating cells (LIC).

By "eradicating quiescent leukemia-initiating cells (LIC)" is meant that the combination of the invention is able to suppress the subset of leukemia initiating cells and therefore at the origin of relapses.

The capacity of the combination of the invention to suppress LIC can be measured by various methods well known to the person skilled in the art. For example, this capacity can be estimated by the measure the reduction of stemness of treated cells with the combination of the invention comparative to no treated cells as described in the Example 7 and FIG. 6 and also in Passegue et al (2005).

Combination of a DNA Methylation Inhibitor with a Vitamin D Receptor Agonist, for Use in Increasing, Restoring or Enhancing Sensitivity to a Chemotherapeutic Drug in a Patient Suffering from Cancer Inventors found that targeting VDR signaling restores sensitivity to chemotherapy by eradicating LIC in AML models. LIC are a subset of leukemic cells in the bulk leukemia population bearing resistance to chemotherapy and therefore at the origin of relapses.

The present invention also provides a combination of
i. a DNA methylation inhibitor; and
ii. a Vitamin D receptor agonist,
for simultaneous or sequential use in increasing, restoring or enhancing sensitivity to a chemotherapeutic agent in a patient suffering from cancer.

Therefore, the present invention also provides a combination of
i. a DNA methylation inhibitor (as defined here above); and
ii. a Vitamin D receptor agonist (as defined here above), and
iii. a chemotherapeutic drug that is an anti-mitotic agent; for simultaneous or sequential use in the treatment of a drug resistant cancer in a patient suffering from cancer.

The present invention also provides a combination of a DNA methylation inhibitor; a Vitamin D receptor agonist and a chemotherapeutic drug that is an anti-mitotic agent, for use in the prevention of tumor relapse in a patient suffering from cancer.

The composition according to the invention may be used in the treatment of drug resistant cancer or in the prevention of tumor relapse in a patient suffering from cancer. Preferably, the drug resistant cancer is a solid tumor (expressing vitamin D receptor) or a hematopoietic malignancy.

In one embodiment, the drug resistant cancer is a solid tumor (expressing vitamin D receptor) selected from the group consisting of: breast cancer, pancreatic cancer, ovary cancer, head-and-neck cancer, colon cancer, colorectal cancer, prostate cancer, stomach cancer and non-small-cell lung carcinoma.

In a preferred embodiment hematopoietic malignancy is selected from the group consisting of acute myeloid leukemia.

In another preferred embodiment, the DNA methylation inhibitor is azacytidine.

In still another preferred embodiment, Vitamin D receptor agonist is Vitamin D3 or inecalcitol.

By a "chemotherapeutic drug" is meant a drug that has proved its efficacy for the treatment of cancer, namely a drug having a marketing approval or a drug undergoing clinical or preclinical trial for the treatment of cancer.

By an "anti-mitotic agent", also referred as a "spindle poison" or a "mitosis poison", is meant an agent that is capable of slowing down and/or inhibiting mitosis. Such anti-mitotic agents can for example stabilize tubulin and thus "froze" the mitosis process (as in the case of most taxanes), or destroy mitotic spindles (as in the case of most vinca alkaloids).

In a preferred embodiment, the chemotherapeutic drug is a taxane. The taxanes are diterpenes that were originally derived from plants of the genus *Taxus*. Now, they are usually synthesized. Taxanes have been used to produce various chemotherapy drugs such as, e.g., paclitaxel (Taxol), docetaxel (Taxotere) and cabazitaxel. These taxanes, and especially paclitaxel (Taxol), are preferred chemotherapeutic drugs that can be used in the frame of the present invention.

Alternatively, the chemotherapeutic drug may be a vinca alkaloid such as, e.g., vinblastine, vincristine, vindesine or vinorelbine.

The chemotherapeutic drug may also be an anti-mitotic agent that is neither a taxane nor a vinca alkaloid, such as e.g., colcemid, colchicine or nocodazole.

The combination of a DNA methylation inhibitor, a Vitamin D receptor agonist and a chemotherapeutic drug that is an anti-mitotic agent, may either be administered simultaneously to the patient, or sequentially. When the administration is sequential, the combination of the DNA methylation inhibitor; and the Vitamin D receptor agonist is preferably administered prior to the chemotherapeutic drug that is an anti-mitotic agent in order to sensitize the patient.

In addition to the anti-mitotic agent and the combination of a DNA methylation inhibitor and a Vitamin D receptor agonist, the treatment regimen of the patient may further comprise surgery, radiotherapy, hormonetherapy, immunotherapy, and/or administration of other chemotherapeutic drugs.

Since the combination of a DNA methylation inhibitor and a Vitamin D receptor agonist sensitizes cancer cells to anti-mitotic agents, the anti-mitotic agents may advantageously be used at lower doses than in a treatment regimen wherein it is administered alone.

Therefore, in a preferred embodiment of the combination according to the invention, the chemotherapeutic drug is for use at a low dose, i.e. at a lower dose than the dose recommended when said drug is administered without said combination of a DNA methylation inhibitor; and a Vitamin D receptor agonist.

The skilled in the art can immediately determine a low dose for a given chemotherapeutic drug. Such a low dose notably depends on the cancer to be treated and on the therapeutic protocol.

In the frame of the present invention, by "low dose" is meant a dose that is inferior to the recommended dose that would be given to the patient when the chemotherapeutic drug is administered in the absence of the combination of a DNA methylation inhibitor; and a Vitamin D receptor agonist. Said low dose is preferably inferior of at least 10%, 15%, 20%, 25% or 50% to the recommended dose.

The recommended dose that would be given to the patient when the chemotherapeutic drug is administered in the absence of the combination of a DNA methylation inhibitor; and a Vitamin D receptor agonist is known to the skilled person. Such a recommended dose can for example be found in the information provided by the authorities delivering marketing authorizations (e.g. in the EPARs published by the EMEA).

As an illustrative example, it will be described here below what is meant by a low dose of docetaxel.

For example, for the treatment of patients with locally advanced or metastatic breast cancer, the recommended dose of docetaxel is 100 mg/m2 in monotherapy. Therefore, a low dose of docetaxel, in the frame of the treatment in monotherapy of patients with locally advanced or metastatic breast cancer, is a dose inferior to 100 mg/m2, preferably inferior to 90 mg/m2, 75 mg/m2 or 50 mg/m2.

In contrast to this, when docetaxel is used as an adjuvant treatment of operable node-positive and node-negative breast cancer, the recommended dose of docetaxel is 75 mg/m2 administered 1-hour after doxorubicin 50 mg/m2 and cyclophosphamide 500 mg/m2 every 3 weeks for 6 cycles (TAC regimen). More generally, docetaxel is usually administered at 75 mg/m2 when associated with another drug (e.g. cyclophosphamide or capecitabin) or when the patient is at risk of not tolerating an aggressive chemotherapy. Therefore, a low dose of docetaxel, when associated with another drug or when the patient is believed not to tolerate an aggressive chemotherapy, is a dose inferior to 75 mg/m2, preferably inferior to 50 mg/m2, 40 mg/m2 or 30 mg/m2.

As another illustrative example, it will be described here below what is meant by a low dose of paclitaxel (Taxol).

Paclitaxel is usually administered at 80 or 90 mg/m2 once a week (e.g. on day 1, 8, 15, and then on day 28 and each following week, optionally in combination with other drugs). Therefore, a low dose of paclitaxel is a dose inferior to 80 mg/m2, preferably inferior to 70 mg/m2, 60 mg/m2, 50 mg/m2 or 40 mg/m2.

In a further embodiment the present invention also provides a combination of
iii. a DNA methylation inhibitor; and
iv. a Vitamin D receptor agonist,
for simultaneous or sequential use in increasing, restoring or enhancing sensitivity to a chemotherapeutic agent in a patient suffering from hematopoietic malignancy said combination being capable of eradicating quiescent leukemia-initiating cells (LIC).

Therefore, the present invention also provides a combination of
i. a DNA methylation inhibitor (as defined here above); and
ii. a Vitamin D receptor agonist (as defined here above), and
iii. a chemotherapeutic drug that is an anti-mitotic agent;
for simultaneous or sequential use in the treatment of a drug resistant cancer in a patient suffering from hematopoietic malignancy said combination being capable of eradicating quiescent leukemia-initiating cells (LIC).

Pharmaceutical Composition and Therapeutic Method

The present invention also provides a pharmaceutical composition comprising:
i. a DNA methylation inhibitor (as defined here above),
ii. a Vitamin D receptor agonist (as defined here above); and
iii. a pharmaceutically acceptable carrier and
iv. optionally a chemotherapeutic drug (as defined here above).

The expression "pharmaceutically acceptable carrier" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen according to the invention depend upon the condition to be treated, the severity of the illness, the age, weight, and sex of the patient, etc.

Pharmaceutical compositions formulated in a manner suitable for administration to humans are known to the skilled in the art. The pharmaceutical composition of the invention may further comprise stabilizers, buffers, etc.

The compositions of the present invention may, for example, be formulated and used as tablets, capsules or elixirs for oral administration, suppositories for rectal administration, sterile solutions or suspensions for administration by injection.

The choice of the formulation ultimately depends on the intended way of administration, such as e.g. an intravenous, intraperitoneal, subcutaneous or oral way of administration, or a local administration via tumor injection.

The pharmaceutical composition according to the invention may be a solution or suspension, e.g. an injectable solution or suspension. It may for example be packaged in dosage unit form.

In a preferred embodiment, the taxane of the invention is preferably administered by the intravenous route, the statin of the invention is preferably administered by the oral route.

The present invention also provides a pharmaceutical composition comprising:
i. a DNA methylation inhibitor (as defined here above),
ii. a Vitamin D receptor agonist (as defined here above); and
iii. a pharmaceutically acceptable carrier and
iv. optionally a chemotherapeutic drug (as defined here above).
for use in the treatment of a patient suffering from drug resistant cancer and/or in the prevention of tumor relapse in a patient suffering from cancer.

The pharmaceutical composition according to the invention can be use in the treatment of drug resistant cancer or in prevention of tumor relapse in a patient suffering from cancer. Preferably, the cancer drug resistant cancer is solid tumor (expressing vitamin D receptor) or a hematopoietic malignancy.

In one embodiment, drug resistant cancer is a is a solid tumor (expressing vitamin D receptor) selected from the group consisting of: breast cancer, pancreatic cancer, ovary cancer, head-and-neck cancer, colon cancer, colorectal cancer, prostate cancer, stomach cancer and non-small-cell lung carcinoma.

In one embodiment hematopoietic malignancy is acute myeloid leukemia.

In preferred embodiment, the DNA methylation inhibitor is azacytidin.

In preferred embodiment, Vitamin D receptor agonist is Vitamin D3 or inecalcitol.

The present invention further provides a methods of treating an individual in need thereof, said method comprising the step of administering an effective amount of:
a DNA methylation inhibitor (as defined here above),
a Vitamin D receptor agonist (as defined here above); and
optionally a chemotherapeutic drug that is an anti-mitotic agent;
to an individual in need thereof.

The drugs are administered in an "effective amount", i.e. in an amount sufficient to treat the cancer. It will be appreciated that this amount will vary with the effectiveness of therapeutic agent(s) employed, with the nature of any carrier used, with the seriousness of the disease and the age of the patient. The determination of appropriate amounts for any given composition is within the skill in the art, through standard series of tests designed to assess appropriate therapeutic levels.

By "individual in need thereof" is meant an individual suffering from cancer, more specifically from drug resistant cancer or an individual that is in remission after having suffered from cancer.

In the frame of the present invention, the individual preferably is a human individual.

The term "treating" is meant to encompass both therapeutic and prophylactic methods, i.e. a method aiming at curing, improving the condition and/or extending the lifespan of an individual suffering from the cancer. More specifically from drug resistant cancer It also refers to methods aiming at preventing the tumor relapse in a patient suffering from cancer.

The invention will be further illustrated by the following figures and examples. However, these examples and figures should not be interpreted in any way as limiting the scope of the present invention.

FIGURES

FIG. 1. VDR expression is associated with differentiation and survival in AML. (A-B) VDR expression tracks with myeloid differentiation in AML and healthy samples.

(A) Retrospective analysis of a genebank dataset study (GSE12417; n=163) showing VDR expression according to FAB subtype in a cohort of normal karyotype AML patients. Results are presented as mean±SEM (*p<0.05, p<0.01, *p<0.001). (B) Retrospective analysis of a genebank dataset study (GSE9476 series) showing VDR expression in healthy samples (including bone marrow (BM) CD34+ cells, n=8; CD34+ cells purified from G-CSF-mobilized donors, n=8; bone marrow nuclear cells (BMMC), n=10; peripheral blood mononuclear cells (PBMC), n=10) and leukemic blasts from AML patients classified according to their FAB subtype (AML0-2, n=8; AML4-5 n=9). Results are presented as mean±SEM (*p<0.05, p<0.01, *p<0.001). (C-D) Limited myeloid differentiation in VDR-deficient transformed cells. (C) Bone marrow hematopoietic precursors from VDR-/- and wild-type mice (Balb/c background) were transduced with retrovirus coding for MLL-ENL, MLL-AF9 or FLT3-ITD. Cell differentiation was evaluated by flow cytometry using CD11b pan-myeloid and F4/80 monocyte markers. Results are presented as mean±SEM (n≥3 mice per group; *p<0.05, p<0.01, *p<0.001). (D) Cell morphology (May-GrünwaldGiemsa/MGG staining) from cells generated in (C). (E-G) VDR and VDR-targeted gene expression correlates with AML prognosis. (E) Overall survival of patients from GSE12417 series (a poll of AML4 or AML5 subtypes n=62) according to VDR expression. Log-rank analysis comparing different groups of patients (separated in tertiles) according to the relative VDR expression (low VDR expression (n=21, A line); medium VDR expression (n=20, B line) and high VDR expression (n=21, C line)). (F-G) Event free survival (EFS) (F) and overall survival (OS) (G) log-rank analysis according to CAMP expression (separated in quartiles, high n=23 (A line) n=23 low (C line) n=90 and median survival of the patient cohort (B line) n=90 are shown). Data were obtained from the Castaigne et al study (Castaigne et al., 2012).

FIG. 2. Oncogene transformation of VDR-/- is associated with increased frequency of hematopoietic progenitors and increased stemness.

(A) Increased frequency of LSK cells in VDR-/- transformed cells (A) up-representative dot-plots of Lin-Sca-1+ KIT+(LSK cells from wild-type and VDR-/- bone marrow cells following leukemic transformation with MLL-AF9 oncogene. (A) down-quantification of LSK+ cells in wild-type and VDR-/- cellstransduced with retrovirus coding for MLL-ENL, MLL-AF9 or FLT3-ITD. Results are presented as mean±SEM (n≥3 mice per cohort; *p<0.05, p<0.01, *p<0.001). (B) Increased expression of stemness-related genes in VDR-/- transformed cells. Wild-type and VDR-/- FLT3-ITD transformed cells were analyzed for the expression of EVI-1, HOXA-9 and MEIS-1 by qPCR analysis. Results are presented as mean±SEM (n≥3 mice). (C) Increased clonogenic potential of VDR-/- transformed cells. Oncogene transformed wild-type and VDR-/- primary hematopoietic progenitors were plated (30.000 cells/condition) in semisolid methylcellulose media containing cytokines (M-3434) and score following 7 to 10 days of culture. For re-plating assays 30.000 cells were plated for each condition. Histograms represents numbers of colonies (mean±SEM of three independent experiments). Results are presented as mean±SEM (n≥6 mice per cohort; *p<0.05, p<0.01, *p<0.001). (D) Oncogene transformation of VDR-/- cells results in resistance to chemotherapy. Wild-type and VDR-/- transformed cells were mock-treated or treated with cytarabine (1 μM) or Valproic acid (VPA; 1 mM) for 72 h. Cell viability was evaluated by The determination of ATP content by luminescence. Results are presented as mean±SEM (n≥3 mice per cohort; *p<0.05, p<0.01, *p<0.001).

FIG. 3 VDR inactivation increased myeloid precursors engaged in monocyte differentiation and increased longevity of LSK cells.

(A-C) In steady-state conditions VDR-deficient mice present normal numbers of wite blood cells (WBC), monocytes and granulocytes. WBC (A), granulocytes (C) and monocytes (C) numbers in 8 to 16 weeks old wild-type (n=14) and VDR-/- (n=11) mice. Data are presented as mean±SEM. (D-E) In steady-state conditions VDR-deficient mice present normal cellularity in bone marrow and spleen. Bone marrow (D) and spleen (E) cellularity of 24 weeks old wild-type (n=6) and VDR-/- (n=6) mice. Data are mean±SEM. (F) Increased numbers of hematopoietic progenitors in VDR-/- mice. Multiparametric flow cytometry quantification of hematopoietic progenitor cells populations in the bone marrow of wild-type and VDR-/- 12 weeks old mice (n=5-8 per group). Lineage restricted progenitors (LRP), common myeloid progenitors (CMP), Monocyte-macrophage progenitors (MMP), common lymphoid progenitors (CLP). (G) Reduced numbers of monocyte progenitors in VDR-/- mice. CFC assays of bone marrow cells from wild-type and VDR-/- mice. Results are presented as mean±SEM (n≥4 mice per cohort; *p<0.05, p<0.01, *p<0.001). (H) Increased numbers of LSK, long-term (LT) and short-term (ST) hematopoietic stem cells (HSC) in VDR-/- mice. Multiparametric flow cytometry quantification of hematopoietic precursors cells populations in bone marrow of 12 weeks old wild-type and VDR-/- mice (n=5-8 animals per group). LSK, LK, LT-HSC, ST-HSC, populations. The proportion of a given population among total viable bone marrow cells is indicated. (H) Hematopoietic precursors from VDR deficient mice presented an increased quiescent status. Cell cycle analyses performed by Ki67 and PI labeling from bone marrow LSK cells from wild-type and VDR-/- mice (n=6 animals/group) left-representative histogram; right-mean±SEM percentages of G0 cells are plotted. (H) Hematopoietic precursors from VDR deficient mice presented decreased ROS levels. CM-H2DCFDA labeling of bone marrow LSK cells from cells from wild-type and VDR-/- mice (n=4 animals per group). left-representative histogram; right-mean±SEM percentages of ROS high cells are plotted.

FIG. 4. Promoter hypermethylation limits VDR expression in AML cells and VDR-deficient cells are resistant to hypomethylation agents.

(A) Schematic representation of the VDR promoter. 5'-CpG-3' islands present in VDR promoter (region ranging from -1035 to -75+ bp relative to the exon 1a transcriptional start codon) represented by dashes. NF-Kb, SP1 and AP-2 binding sites are indicated (B) VDR promoter is modified by methylation in AML. (B-C) hypomethylating agents modify VDR promoter methylation in AML cells. Leukemic cells from AML patients (n=3 were treated or not with 5-azacytidine (5-AZA; 1 μM) for 96 hours. Histogram shows methylation specific PCR (MSP) for the VDR promoter (region comprising −1035 to −75 bp from start codon). (C) THP1 cells were treated or not with 5-AZA (1 μM) for 96 hours and genomic DNA was transformed by bisulfite. High Resolution Melt PCR for the VDR promoter (region comprising −1035 to −75 bp from start codon) was performed. Non-treated cells (A line) 5-AZA-treated cells (B line). (D) VDR−/− transformed cells are resistant to 5-AZA treatment. MLL-ENL transformed wild-type and VDR−/− cells were treated or not for 72 h with growing concentrations of 5-AZA. Cell viability was evaluated by ATP assay. Results are presented as mean±SEM (ns not significant, *p<0.05, p<0.01, *p<0.001). (E-F) 5-AZA treatment induces VDR and VDR-target genes expression in AML cell lines. HL60 were mock-treated or treated with 5-AZA (5 μM) or Vitamin D (1000 μM; as positive control) for 6 hours. (E) VDR or VDR-target genes (CAMP and CYP24A1) expression was evaluated by qPCR. Results are presented as mean±SEM. (G) 5-AZAtreatment induces VDR-target genes expression in leukemic cells from AML patients. Primary cells (n=3 patients) were mock-treated or treated with 5-AZA (5 μM) or inecalcitol (INEC; 10 μM) or both for 6 hours. VDR or VDR-target genes (CAMP and CYP24A1) expression was evaluated by qPCR. Results are presented as mean±SEM.

FIG. 5. 5-AZA and VDR analogs synergize to promote AML cells differentiation and reduce tumor growth.

(A) Structural formulas of 1-25 dihydroxyvitamin D3 (VD) and VDR agonist Inecalcitol. http://www.chemblink.com/products/163217-09-2.htm. (B-D) Hypomethylating agents synergize with VDR agonists to promote myeloid differentiation and VDR activity. (B) U937 cells were mock-treated or treated with 5-AZA (5 μM), INEC (10 nM) or both for 72 hours. CD11b and CD14 expression was evaluated by flow cytometry. Results are presented in fold increase compared to vehicle Histograms are mean±SEM (n≥10; *p<0.05, p<0.01, *p<0.001). (C) HL60 cells were mock-treated or treated with 5-AZA (5 μM), with Vitamin D (300 nM) or INEC (10 nM) for 16 hours. Granocyte differentiation genes (PRTN3 and NE) and monocyte differentiation genes (TREML2 and SERPINB8) were accessed by qPCR. Results are presented as mean±SEM. (D) U937 cells were mock-treated or treated with 5-AZA (5 μM), INEC (10 nM) or both for 16 hours. VDR activation was evaluated by immunoblot using anti-phospho-VDR specific antibodies. VDR antibodies were used to control protein loading. (E-G) Combined Hypomethylating agents/VDR agonists therapy impairs tumor growth. (E) HL60 cells were mock-treated or treated with 5-AZA (5 μM), with INEC (10 nM) or both for 16 hours. Cell cycle analyses were performed by topro-3 labeling. Results are presented as mean±SEM. Percentages of G1, S and G2 phases cells are plotted (n≥3; *p<0.05, p<0.01, *p<0.001). (F) Expression of cell cycle regulator genes p15, p21 and p27 was evaluated by qPCR. Results are presented as mean±SEM. (G) Kaplan-Meier plot of survival of mice treated with vehicle (PBS), 5-Acytidine (5 mg/kg intraperitoneally three times a week for five injections) and or INEC (20 μg per mice intraperitoneally, three time a week) after subcutaneous xenograft with U937 cells (n=8 tumors in each group). The p-value was determined using the log-rank test.

Figure 6:
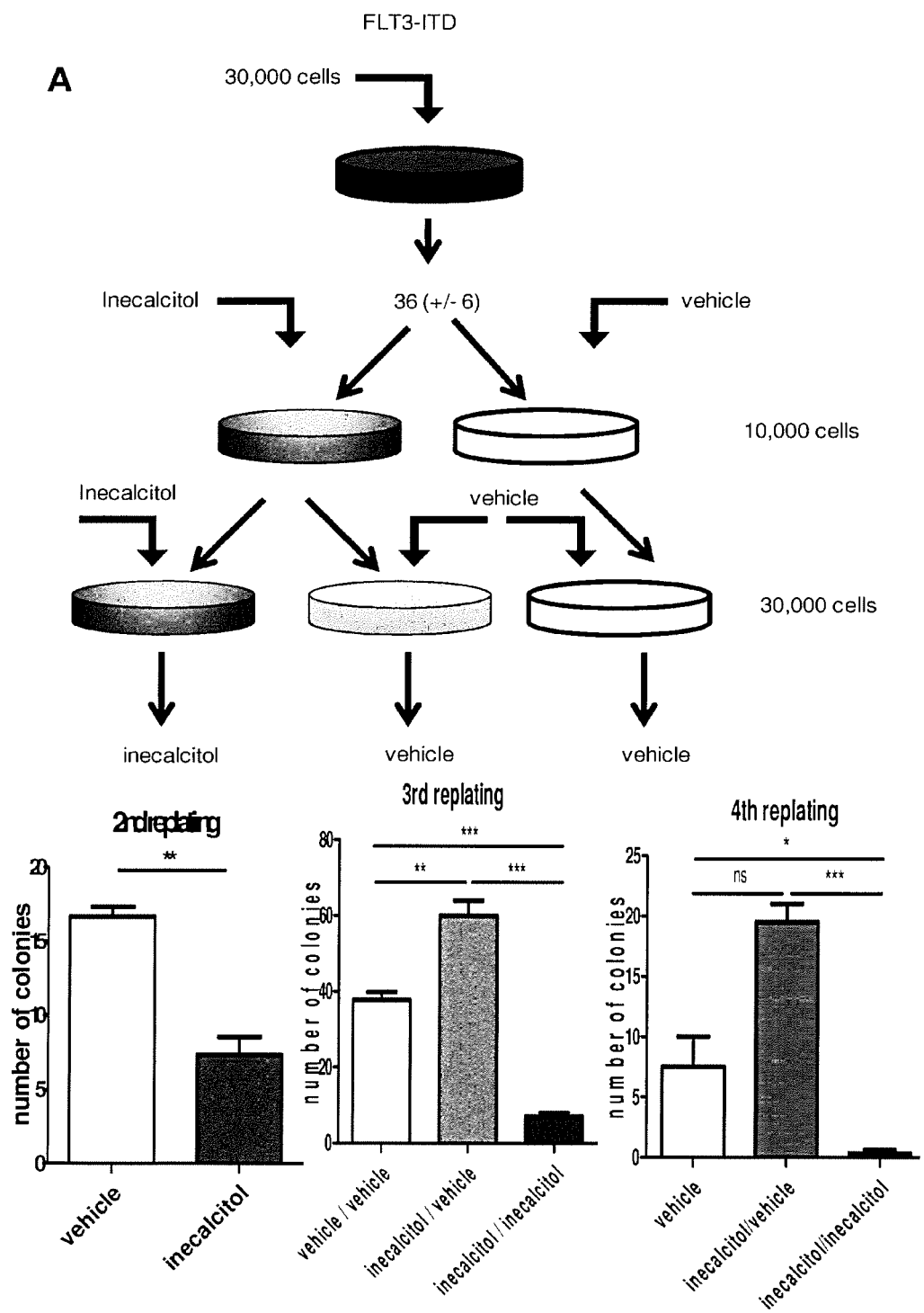
Figure 6:
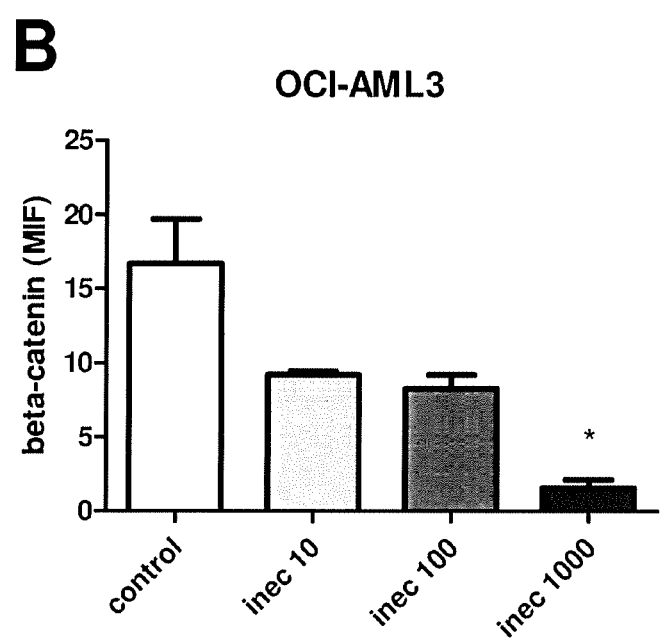

FIG. 6. VDR analogs reduces stemness of AML cells.

(A) Inecalcitol decreases clonogenicity of FLT3-ITD of transformed cells. FLT3-ITD-transformed bone marrow hematopoietic progenitors were plated (30.000 cells/condition) in semisolid methylcellulose media containing cytokines (M-3434) containing or not INEC (10 nM) and scored following 7 to 10 days of culture. For re-plating assays 10-30.000 cells were plated (as indicated) in the presence or in the absence of INEC (10 nM) for each condition. Histograms represents numbers of colonies (mean±SEM of three independent experiments). Results are presented as mean±SEM of 4 independent experiments. (B) VDR agonists inhibits β-cathenin pathway OCI-AML3 cells were mock-treated or treated with growing concentrations of INEC (10, 100 or 1000 nM) for 48 hours. β-catenin expression was evaluated by flow cytometry.

EXAMPLES

Example 1: Experimental Procedure

Clinical Samples and Cell Lines

Peripheral bloods cells were obtained from AML patients after obtaining their written informed consent and approval by Necker ethic committee. Peripheral blood was collected at the initial diagnosis before the administration of any treatment. Mononuclear cells were purified by Ficoll-hypaque (PAA laboratories) density centrifugation and resuspended in DMEM (Invitrogen) supplemented with 15% FCS (Biowest), 100 ng/ml stem cell factor, 10 ng/ml IL-3 and 25 ng/ml FLT3-L (Peprotech). Promyeloblastic (HL-60), myelocytic (OCI-AML3), monoblastic (THP1 and U937). Cells were cultured in RPMI-1640 medium (Invitrogen) supplemented with 10% Foetal Calf Serum (FCS) and antibiotics.

Flow Cytometry

Flow cytometric analyses were performed according to standard protocols. In brief, single-cell suspensions were resuspended in flow cytometry buffer (PBS without Mg2+ or Ca2+ (PBS−/−), 0.5% FCS, 0.1% Sodium azide (pH 7.4). Viable cell numbers were determined by cell counting after trypan blue staining. For flow cytometric analyses the Fc blocking was performed with 24G2 and cells immunostained with fluorophore-linked antibodies (BD Biosciences, eBioscience, Biolegend). For immunostaining of lineage (Lin)-positive cells, a cocktail containing biotin-labelled primary antibodies against CD5, B220, CD11b, 7-4, Gr-1 and Ter-119 (BD Biosciences) was used, followed by staining with streptavidin-linked fluorophore-labelled secondary antibodies.

Intracellular staining to Ki-67 (clone, biolegend) was performed with the use of Fix and Perm kit (BD Biosciences). Stained cells were analysed with the use of a FACS LSR Fortessa. Cell sorting was performed with a FACS Aria II (BD Biosciences).

ROS levels evaluated by labeling cells (1.106) for 30 minutes at 37° C. with 10 μM of CM-H2DCFDA (5-(and-6)-chloromethyl-29,79-dichlorodihydrofluorescein diacetate, acetyl ester) redox-sensitive probe (Abcam).

Preparation of Recombinant Retroviruses

Plasmids encoding human MLL-ENL or MLL-AF9 or FLT3-ITD (kindly given by Dr Patrice Dubreuil, Cancerology Research Centre of Marseille (CRCM), France) all cloned in MSCV-IRES vector. Retroviral production was performed by transient transfection of retroviral packaging cells (Plat-E, Cell Biolabs) by the use of Lipofectamine LTX plus (Invitrogen). Retroviruses released into the culture supernatants were used for infection of mouse hematopoietic cells with the use of retronectin (Takara) coated plaques according to the manufacturer procedure.

Generation of AML Model

Murine MLL-ENL AML was initiated as described (Somervaille et al., 2009). Briefly, BM cells were flushed from the long bones of four to eight week-old mice 5 days after they had been injected with 50 mg/kg of 5-FU. Cells were incubated for 48 hours in DMEM with 15% FCS, 10 ng/ml IL3, 50 ng/ml SCF and 10 ng/ml IL6 (Peprotech) at 37° C. to promote cell cycle entry. Cells were then spinoculated with retroviral supernatant on retronectin (Takara) according to the manufacturer's instructions for 48 hours at 37° C.

Immediately following spinoculation, cells were injected by retroorbital vein of sublethally irradiated mice (350 cGy; 106 cells per mouse). Leukemic bone marrow cells and splenocytes were recovered from sick mice (typical latency 60-100 days) and cryopreserved for subsequent experiments.

Cell Cycle Analysis

For Ki-67/PI staining, the cells were first treated with Fix and Perm reagents according to the manufacturer's instruction (BD Biosciences), incubated with Ki-67 antibody (16A8, Biolegend), and then washed and resuspended in PBS with 5 μg/ml RNaseA and PI. Stained cells were analyzed using a FACS Fortessa (BD Biosciences).

Cell Death Assays.

Cells were stained with Annexin V and Propidium Iodide according to the manufacturer's instructions (BD Biosciences) and then analyzed by flow cytometry to assess levels of apoptosis.

Cells were seeded into 96-well plates, and then returned to the 37° C. incubator after the addition of different reactives or vehicle controls DMSO and ethanol if not otherwise stated. Celltiter Glo reagents (Promega) were added after 48 to 96 hours to determine cell viability by measuring ATP levels. The luminescence of each sample was determined in a plate-reading Tecan Infinimite M1000 Pro (Tecan) as directed by manufacturer.

RT and Real-Time PCR Analysis

Total RNA was extracted, purified using RNeasy kit (Qiagen) and subjected to RT (iScript Reverse Transcriptase supermix, Bio-Rad). Quantitative real-time PCR was performed using a CFX96 PCR system (Bio-Rad), and PCR products were quantified using Ssofast Eva Green (Bio-Rad). The results of the real-time quantitative PCR were analyzed according to the MIQE guidelines (Bustin S A Clin Chem 2009) using the delta-delta Cq method (Livak 2001).

Methylation Analysis

In order to analyze methylation levels from the cell lines of interest, total genomic DNA (gDNA) was isolated from each cell line using the QIAamp DNA Micro Kit (Qiagen) according to the manufacturer's instructions. Following purification, 2 μg of gDNA from each cell line were subjected to sodium bisulfite treatment via the EpiTect Bisulfite Kit (Qiagen) according to the manufacturer's instructions. Each region of interest was PCR amplified using. Primer pairs were designed using the web-based software MethPrimer and their optimal annealing temperature was determined via gradient PCR.

Methylation Specific PCR (MSP) analysis was carried out using primers corresponding to the VDR promoter region sequences. One can design PCR primers to distinguish methylated from unmethylated DNA in bisulfite modified DNA, taking advantage of the sequence differences resulting from bisulfite modification.

Real-time Methylation Sensitive High Resolution Melting Curves analysis (MS-HRM), composed of real-time HRM analyses, was conducted. PCR amplification and HRM analysis were carried out sequentially on a CFX96 PCR system (Bio-Rad). HRM analysis was conducted with temperature ramping from 60 to 95° C. The ratio was calculated on the basis of the 2 standard curve relative quantification methods. The HRM curves were normalized by the software to allow comparison between the samples. All the samples were analyzed in duplicate.

Tumor Xenografts

For tumor establishment, U937 or OCI-AML3 cells as indicated were mixed with Matrigel (BD Biosciences) (1:1, vol/vol) and injected subcutaneously ($5\times10^6$/flank) into 10-week old female athymic Nude mice (Janvier laboratories, France). The mice were then injected i.p. with 5-Azacytidine (Celgene) (5 mg/kg on day 5, 7, 9, 11 and 13), Inecalcitol (Hybrigenics) (20 μg/day 3 times a week), and the combination of 5-Azacytidine and Inecalcitol or PBS as a vehicle control. The tumor growth was measured as previously described (Lepelletier 2007).

Methylcellulose Colony-Forming Assays

Colony formation by transformed or not mouse cells was examined with the use of Methocult medium (MethoCult GF M3434, StemCell Technologies). WT and VDR−/− cells infected were collected from BMT with oncogene or not and transferred to Methocult medium. Colonies were scored one week after plating for determination of the number of colonies. For serial plating cells were collected from methylcellulose, washed once in PBS, counted and replated in Methocult. For some experiments, 10 nM Inecalcitol (hybrigenics) was added to the culture medium.

Human Samples Microarray Analysis

AML and HSPC samples used in this study have been described previously (Metzeler et al Blood., 2008) and are available at the GEO database under accession number. GSE12417. Analysis was performed using R 2.14.0 and BioConductor. Raw data were generated using the RMA package. For comparison of different array sets, raw expression data were normalized to the mean of control GAPDH probe sets.

Statistical Analysis

The data are expressed as the mean±SEM. Statistical analyses were performed using Prism 5 software (GraphPad Software, Inc.). We used the Student's t test or the Mann-Whitney test to compare two groups, and multigroup comparisons were made using a one-way ANOVA followed by a post-hoc Bonferroni test. We used the Kruskal-Wallis test followed by a post-hoc Dunn test for nonparametric comparisons, where indicated. To compare tumor-free animal curves, the Log-rank test was used. The results were considered statistically significant at a p-value <0.05 (*), <0.01 (), or <0.001 (*).

Results

Example 2: VDR Expression is Associated with Monocyte Differentiation and Survival in AML Induction of VDR signaling has been shown as therapeutic target in AML (Elstner et al., 1994; Kim et al., 2012; Munker et al., 1986). However, the role of VDR in AML pathology is unknown. In order to evaluate consequences of VDR expression/activity in AML we conducted a retrospective analysis of a published gene expression dataset (GSE12417 series, contributed by Dr. K. H. Metzeler, University of Munich, Munich, Germany) (Metzeler et al., 2008) that comprised normal karyotype patients (n=163) classified according to the French-American-British (FAB) system (Bennett et al., 1976). We found in this patient cohort that VDR expression was increased in AML subtypes presenting features of monocyte differentiation (AML4 and AML5) compared to immature/undifferentiated AML subtypes (AML0, AML1 and AML2) (FIG. 1A). Expression of other monocyte differentiation markers such as CD14 or CSF1R (Friedman, 2002) were not different between AML0-2 and AML4-5 subtypes suggesting that differences in expression according to AML subtype were not restrained to markers of monocyte differentiation. Evaluation of the expression of SERPINB8 (a VDR-targeted gene) confirmed that increased VDR expression in AML5 patients was associated with induction of VDR signaling. Therefore, undifferentiated/immature AML subtypes presented a decreased VDR expression and VDR activity compared to AML subtypes engaged in the monocyte pathway.

1,25-dihydroxyvitamin D3 (VD) is well known by its ability to induce myeloid progenitor cells to differentiate into monocytes (Munker et al., 1986; Nagler et al., 1986). However, distribution of VDR expression during normal hematopoiesis was not reported. To further gain insights in variations on VDR expression in samples from healthy individuals and AML samples we conducted an additional retrospective analysis (GSE9476 series contributed by Dr. Derek L Stirewalt, Clinical Research Division, Seattle, Wash., USA) (Stirewalt et al., 2008). Analysis from this study confirmed an increased VDR expression in AML4-5 subtypes in comparison to AML0-2 subtypes (FIG. 1B). This analysis also showed that VDR expression did not differ between AML0-2 patients and CD34+ cells purified from bone marrow or from G-CSF-mobilized patients (FIG. 1B). Moreover, VDR expression was similar between bone marrow nuclear cells (BMMC) and AML4-5 subtypes (FIG. 1B) but VDR expression in AML4-5 subtypes was decreased in comparison to peripheral blood mononuclear cells (PBMC) (FIG. 1B). Further investigation of VDR expression during human normal hematopoiesis (http://servers.binf.ku.dk/hemaexplorer/) confirmed that VDR expression was low in hematopoietic progenitors and myeloid precursors and then increased in fully differentiated monocytes. Therefore these studies suggested that VDR expression tracks with myeloid differentiation in healthy cells, that VDR expression in AML0-2 subtypes is similar to that observed in CD34+ cells and that AML-4-5 subtypes presented a decreased VDR expression compared to mature mononuclear cells presented in the bloodstream.

To gain insights in cellular consequences of decreased VDR expression in AML cells we moved to minimal cellular models by inducing transformation of hematopoietic precursors from VDR knockout mice (VDR–/–) with AML and myeloproliferative neoplasm (MPN) oncogenes. Bone marrow precursors were transformed with retrovirus coding for MLL-ENL, MLL-AF9 fusion proteins or FLT3-ITD construct and monocyte differentiation was evaluated by the expression of CD11b and F4/80 by flow cytometry and by cell morphology (May-Grünwald Giemsa/MGG staining). Transduction of VDR–/– hematopoietic precursors resulted in fewer CD11b+ F4/80+ double positive cells and those cells presented an immature morphology when compared to wild-type transduced cells (FIG. 1C-D). Therefore, inactivation of VDR expression is sufficient to limit myeloid differentiation in AML/MPN models.

To further investigate the relevance of variations of VDR expression in AML we correlated the VDR expression to patients' prognosis. Since VDR expression was low in AML0-2 patients we decided to stratify AML4-5 population from GSE12417 series (n=62 patients) according to their baseline VDR expression levels. Overall survival (OS) was evaluated in patients presenting higher VDR expression (third tertile, n=21 patients), intermediate VDR expression (second tertile, n=20 patients) and lower VDR expression (first tertile; n=21 patients). Log-rank analysis of plotted curves showed that patients presenting higher VDR expression presented an increased OS compared to patients presenting lower VDR expression (FIG. 1E). Thus decreased VDR expression correlates to an immature AML phenotype and a worse prognosis in AML4/5.

The relevance of VDR signaling pathway in AML relapse was further evaluated by comparing patients' prognosis to the expression of VDR-targeted genes. For these experiments we used a well defined cohort of patients (Castaigne et al., 2012) (all AML subtypes confounded excepted for AML3 n=90. Patients presenting higher CAMP (Cathelicidin Antimicrobial Peptide, a VDR-targeted gene) expression (n=23, 4rd quartile group) presented an increased event free survival (EFS) and relapse-free survival (RFS) compared to patients presenting lower levels of CAMP (n=23, 1st quartile group) (FIG. 1F-G). Of note, this cohort of patients also revealed an increased VDR expression in AML subtypes presenting features of monocyte differentiation further confirming previous observations from geneset databases GSE12417 and GSE9476. Therefore, VDR/VDR-targeted gene expression is correlated to monocyte differentiation and improved prognosis in AML patients in all AML subtypes.

Example 3: Promoter Methylation Decreases VDR Expression in AML Cells and Demethylating Agents Sensitivity is Dependent on VDR Expression We next sought to evaluate the molecular mechanisms contributing to decreased VDR expression in AML cells which would contribute to impaired monocytic differentiation. Since AML is characterized by an altered methylation profile in CpG islands (Akalin et al., 2012) and VDR promoter has been shown to be modified by methylation (Marik et al., 2010) we evaluated whether methylation would induce VDR silencing in AML. An analysis of the VDR promoter revealed that CpG islands were frequent in VDR promoter and particularly in a region ranging from −75 to −1035 bp of ATG initiation codon (FIG. 4A). We then performed VDR promoter methylation analysis in bisulfite converted genomic DNA from primary AML samples which were treated or not by the demethylating agent 5-AZA. In cells treated by 5-AZA there was a decrease in methylation suggesting that CpG islands in VDR promoter are methylated in AML cells (FIG. 4B). Further methylation-sensitive high resolution melting (MS-HRM) analysis on THP-1 cells confirmed that VDR promoter has a unimodal peak of containing the majority of reads with high levels of methylation and that 5-AZA can revert VDR promoter methylation (FIG. 4C). Studies in AML primary samples confirmed these observations.

We then studied the consequences of VDR invalidation in cell sensitivity to demethylating agents. Dose ranging studies showed that wild-type MLL-ENL transformed cells were sensitive to 5-AZA whereas VDR–/– cells survival was not altered by 5-AZA (FIG. 4D) suggesting that 5-AZA sensitivity is dependent on VDR expression. An evaluation of the functional consequences of epigenic modifier treatment on HL60 cells revealed that VDR expression was 2-fold increased in 5-AZA treated cells whereas both 5-AZA and VD induced the expression of VDR targeted genes (CAMP and CYP24A1) (FIGS. 4E and 4F) suggesting that promoter methylation contributes to VDR inactivation which was further confirmed in AML primary samples (FIG. 4G). Therefore, these data suggest that VDR promoter is methylated in AML cells impairing VD activity and that sensitivity of AML cells to 5-AZA is dependent on VDR expression.

Example 4: Combined Therapy Using Demethylating Agents and VDR Analogs Promotes a Synergistic Effect Inducing Cell Differentiation, Cell Cycle Arrest and Apoptosis Induction in AML Cells Resulting in Decreased Tumor Progression in Mice VDR agonists have been shown to promote monocyte differentiation in AML cells. However, in clinical trials VD and VDR agonists were not able to induce clinical responses because of the occurrence of life-threatening hypercalcemia (Kim et al., 2012). Inecalcitol (INEC) is a highly potent VDR agonist developed to avoid hypercalcemia in patients (Kim et al., 2012; Petrini et al., 1991). Dose-response studies showed that INEC was 1000-fold more effective than VD to promote AML cells differentiation (FIG. 5A). Since VDR expression was shown to be inhibited in AML samples, we postulated that a combined therapy reducing promoter methylation by 5-AZA and VDR agonists would be able to potentiate VDR signaling in AML cells. Whereas 5-AZA and NEC promoted a significant but slight increase in myeloid differentiation (1.3-fold for 5-AZA and 4.5-fold for INEC) the combined therapy promoted a huge increase (8-fold) in the expression of CD11b and CD14 expression in AML cell lines (FIG. 5B). This synergistic effect was also observed in the expression of monocyte differentiation markers (TERML2, SERPINB8) which expression were upregulated in cells treated by combined therapy whereas granulocyte markers expression (NE, PRTN3) were downregulated in comparison to controls suggesting that combined therapy favors monocyte differentiation in the detriment of granulocyte differentiation (FIG. 5C) as previously shown for VD (Callens et al., 2010a). Further morphological analysis confirmed these observations. These results were also confirmed in AML primary samples. As expected the synergistic effect between VDR agonists and demethylating agents was not restricted to 5-AZA since decitabine showed similar results in promoting AML cells differentiation.

Combined AZA/INEC therapy promoted VDR phosphorylation (FIG. 5D) as well as the activation of the downstream MAPK pathway. Whereas the MAPK/ERK and MAPK/JUNK inhibitors completely prevented cell differentiation induced by the combined therapy the MAPK/p38 inhibitor has a lesser effect in decreasing cell differentiation. Thus the combined AZA/INEC therapy induces VDR and MAPK activation which results in AML cells differentiation. Combined AZA/INEC therapy was also effective in inducing a cell cycle arrest and the up-regulation of cyclin-dependent kinase (cdk) inhibitors including p15, p21 and p27 (FIG. 5E-F) and apoptosis of leukemic cell lines further suggesting that the associated therapy would provide strong cell potential anti-leukemic effects.

Moreover, in an in vivo in a mouse tumor xenograft model AZA/INEC therapy resulted in increased survival and decreased the tumor size in xenografted mice compared to control mice (FIG. 5G). The reduced tumor growth was associated with increased numbers of cells undergoing apoptosis and features of cellular differentiation. In this model, we did not observe a significant effect in survival or tumor growth when 5-AZA and inecalcitol were used as a single therapy compared to controls (FIG. 5G). Altogether, these results indicate combined treatment by VDR agonists and 5-AZA synergize to promote VDR signaling pathway which results in impaired growth and apoptosis of AML cells which is effective to prevent tumor burden in AML models.

Example 5: VDR Inactivation Increased Myeloid Precursors Engaged in Monocyte Differentiation and Increased Longevity of LSK Cells Previous studies showed that VDR−/− mice presented normal numbers of circulating monocytes suggesting that VDR is not essential for myeloid differentiation (O'Kelly et al., 2002). Complete blood cells from VDR−/− and wild-type mice analysis in steady-state conditions confirmed and extended these results since no differences were observed in platelets, granulocytes, red blood cells and monocytes numbers between wild-type and VDR−/− mice (FIG. 3A). In addition, there was no difference between VDR−/− and wild-type animals in both bone marrow and spleen cells numbers (FIG. 3B). However, analysis of progenitor cells revealed that lineage restricted progenitors (LRP), common myeloid progenitors (CMP) increased in VDR−/− mice compared to wild-type mice. Monocyte macrophage progenitors (MMP) populations were however decreased in VDR−/− mice compared to wild-type mice (FIG. 3C) suggesting that monocyte differentiation was impaired in VDR−/− mice. In agreement CFC assays revealed that VDR−/− BM presented a decreased ratio of macrophage (M)/granulocyte (G) colonies (FIG. 3D). Therefore VDR−/− mice presented decreased numbers of monocyte progenitors further confirming previous results showing that VDR expression results in cells engaged in monocyte differentiation.

We then evaluated whether VDR inactivation impacts on hematopoietic stem cell (HSC) and hematopoietic progenitor cell (HPC) compartments in VDR−/− mice. Flow cytometric analyses of bone marrow revealed that the lineage negative (Lin-)Sca-1+ KIT+ (LSK) population was increased by approximately 3-fold in VDR−/− mice in comparison with wild-type mice (FIG. 3E). Further investigations in LSK subpopulations showed that both long term HSC (LT-HSC) and short term HCS (ST-HSC) were increased in VDR−/− mice (FIG. 3E).

Levels of reactive oxygen species (ROS) have been shown to control HSC homeostasis and decreased ROS levels were associated to increased HSC longevity whereas high ROS levels were associated with myeloid differentiation (Callens et al., 2010a; Callens et al., 2010b; Jung et al., 2013; Tothova et al., 2007). We evaluated ROS levels in LSK cells by using the ROS indicator CM-H2DCFDA. Analysis of relative ROS levels revealed that VDR−/− mice presented decreased numbers of LSK cells expressing high ROS levels compared to their wild-type controls (FIG. 3F) further suggesting increased longevity in cells deficient for VDR expression.

Since HSC maintenance during steady-state conditions depends upon their quiescent state (Passegue et al., 2005) we searched for differences in cell cycle between wild-type and VDR−/− mice. Flow cytometry labeling with PI and Ki-67 on LSK gated cells revealed that VDR−/− cells had an increase in the percentage of quiescent G0 cells and a decrease in the percentage of cycling G1 and S-G2/M cells (FIG. 3G). Therefore VDR−/− mice have an increased quiescent status and decreased ROS levels which are associated an increased longevity of HSPCs compartment.

Example 6: Oncogenic Transformation of VDR-Deficient Cells Results in AML with Increased Leukemic Stemness Potential To gain further insights in the consequences of impaired monocyte differentiation in VDR−/− cells we decided to scrutiny the phenotype of resulting CD11b-F4/80-transformed cells. We therefore studied the expression of phenotypic markers of hematopoietic progenitors in wild-type and VDR-deficient cells transformed with constructs for FLT3-ITD, MLL-ENL and MLL-AF9 fusion proteins. Multiparametric flow cytometry analysis showed that the frequency of LSK cells was increased in VDR−/− transformed cells in comparison with wild-type transformed cells (FIG. 2A). as previously observed in normal hematopoietic cells In agreement, expression of genes related to the LSK phenotype (EVI-1, HOXA-9 and MEIS-1) and which were downregulated readily from myeloid progenitors commitment (Chen et al., 2008) was increased in VDR−/− transformed cells (FIG. 2B). Thus, inactivation of VDR in oncogene transformed cells results in cells of immature phenotype and with a likelihood LIC potential.

We subsequently examined the role of VDR in the maintenance of the renewing potential of LIC. Oncogene transformed cells were plated in methylcellulose and colonies were counted between days 7 and 10 of culture (FIG. 2D). Wild-type and VDR−/− transformed resulted in a similar colony-forming cells (CFC) numbers in this first round of plating (FIG. 2D). However, following serial replating VDR−/− transformed cells resulted in an increased clonogenic potential compared to wild-type cells (FIG. 2D). Thus, oncogenic transformation of VDR−/− cells results in enhanced clonogenic potential, a feature of LIC.

Therefore, in 3 different models of leukemic transformation with fusion proteins cells able to express VDR bear a more mature phenotype, present reduced LIC compartment and increased sensitivity to chemotherapy compared to VDR−/− cells. Altogether, these data suggested that VDR expression during leukemogenesis can modulates monocyte differentiation of transformed cells and the absence of VDR expression results in AML cells of immature morphology and phenotype and increased stemness.

Example 7: Targeting VDR Signaling Restores Sensitivity to Chemotherapy and Eradicates LIC in AML Models LIC are a subset of leukemic cells in the bulk leukemia population bearing resistance to chemotherapy and therefore at the origin of relapses. Next we explored the efficacy of VDR agonist therapy in targeting LIC cells. To test this hypothesis we transduced bone marrow precursors from wild-type and VDR−/− mice with the FLT3-ITD construct. Cells were plated in semi-solid cultures containing INEC or vehicle as a control (FIG. 6A). Growth of FLT3-ITD transformed cells in methylcellulose containing INEC led to a 5-fold decrease in clonogenic potential compared to vehicle-treated cells (FIG. 6A) and replating assays revealed that INEC treatment induced a progressive loss LIC capacity with virtually no colonies growing at the 4th round of plating whereas vehicle-treated cells kept their clonogenic capacity during serial plating in methylcellulose (FIG. 6A). To further examine is the INEC effect was reversible we divided $2^{nd}$ replating INEC-treated cultures in two groups containing INEC or a vehicle. INEC wash-out reestablished CFC suggesting that continuous treatment with VDR agonists would maintain the selective pressure to eradicate LIC (FIG. 6A). Therefore in vitro colony replating assays suggest that VDR signaling is a major pathway controlling LIC homeostasis and that VDR agonists are able to eradicate LIC.

In line with these observations, in vitro treatment of FLT3-ITD/NPM1 AML blasts (Mupo et al., 2013) with INEC resulted in increased expression of myeloid differentiation markers (FIG. 6B). Mice adoptively transferred with INEC treated cells were not able to develop leukemia. In agreement, biological as well as immunophenotypic markers of leukemia cells were normalized in INEC-treated animals (FIG. 6C). In agreement passive transfer of BM cells from INEC-treated animals resulted in strongly delayed leukemia development in comparison to mock-treated animals (FIG. 6D). Therefore, induction of VDR signaling promotes growth arrest of clonogenic progenitors resulting in decreased LIC longevity and VDR agonists treatment resulted in decreased tumor burden and LIC targeting. Taken together, these data provide a rationale for the therapeutic use of VDR agonist in the treatment of AML.

Example 8: Discussion

Methylation is a frequent process occurring in mammalian genome and genome-wild demethylation is essential for embryo development (Feng et al., 2010). In addition, epigenic modification has been recently observed during somatic cells development and 5'-CpG-3' dinucleotidesdemethylation has been shown to be essential for erythropoiesis progression (Shearstone et al., 2011). However, identification of genes silenced by epigenetic modification influencing the blockage of myeloid differentiation, a feature of AML, was not addressed in details. Our data suggests that inactivation of VDR expression by promoter hypermethylation is a new mechanism associated with differentiation/FAB classification but also with AML progression since VDR/VDR-targeted gene expression was associated with increased patient survival. Our study also identify VDR as a target for hypomethylating agents since VDR−/− transformed cells were resistant to 5-AZA treatment. Therefore, regulation of VDR expression by epigenic modification defines a new role of this nuclear receptor in AML with consequences in hypomethylating agents therapy.

In a recent study with 5,848 AML patients AML0 subtype was associated with decreased relapse-free and overall survival a suggesting that immature phenotype could result in worsened disease outcome (Walter et al., 2013). Our studies in AML patients suggest that VDR repression could be a new gene controlling AML cells differentiation and that VDR under-expression would be a feature of AML0-2 phenotypes. Complementary studies VDR invalidated cells showed that oncogenic transformation with AML oncogenes resulted in cells bearing features of immature phenotype. Therefore our data suggests that VDR would be a new genetic modifier contributing to the expression of different AML subtypes with a potential application in patients' management since increased VDR expression in AML4/5 subtypes was associated with an improved prognosis.

VDR inactivation appeared to be essential for hematopoietic stem cells and myeloid progenitors differentiation control. In agreement, HSCs from VDR−/− mice showed and increased quiescence status and a reduced ability to accumulate ROS which have been both implicated in the protection of HSCs pool from premature exhaustion therefore allowing its long-term maintenance (Amrani et al., 2011; Takubo et al., 2013; Tothova et al., 2007). ROS participates in cell fate decisions which are critical for hematopoiesis and both myeloid differentiation and HSC homeostasis are both dependent of ROS levels. The importance of ROS in hematopoiesis control is highlighted by its conservation throughout evolution in different species ranging from drosophila, mice and humans (Callens et al., 2010a; Owusu-Ansah and Banerjee, 2009; Sasaki et al., 2012). In addition, ROS gradients have been also shown to be essential to maintain the myeloid differentiation (Callens et al., 2010a; Owusu-Ansah and Banerjee, 2009) and therefore inactivation of VDR expression also resulted in limited myelopoiesis. ROS levels were decreased in VDR-deficient cells suggesting the existence of a new pathway controlling HSC homeostasis through the modulation of ROS observed in both human leukemia cells and oncogene transformed mouse cells transformed. Both quiescence of stem cells and the maintenance of myeloid differentiation have been shown to result in MAPK pathway activation in conditions of various stresses (Ito et al., 2006). Our data showing that myeloid differentiation is dependent on VDR signaling through MAPK activation suggests that VDR signaling is a major pathway upstream MAPK activation. Thus, VDR signaling appeared as critical element controlling ROS homeostasis and MAPK signaling with an implication in both normal and malignant hematopoiesis.

The use of DNA demethylation agents have been proposed in MDS and AML therapy but their efficacy as a monotherapy in clinical trials was shown to be limited since although response were encouraging (around 20%) median response durations were low (Fenaux, 2005; Quintas-Cardama et al., 2012; Sekeres et al., 2010). Here, we show that combined use of demethylating agents and VDR agonists resulted in a potent activation of VDR signaling pathway which limited leukemia progression and abolished the clonogenic potential of LIC. Therefore, association of demethylation agent therapies with VDR agonists would allow to improve the efficacy of DNA hypomethylating agents in AML. Further clinical trials would be able to confirm this hypothesis in AML patients.

Death in AML usually occurs from a progressive disease following relapse. Relapses are associated with clonal evolution because of the selective pressure exerted by chemotherapy and it is believed to be associated with leukemia initiating cells (characterized by longevity and resistance to chemotherapy because of their limited cell cycling) in the bulk of the tumor mass. We show that induction of VDR signaling results in monocyte differentiation, apoptosis and sensitivity to chemotherapy since oncogene transformed VDR−/− cells presented impaired differentiation, increased resistance to chemotherapy apoptosis suggesting that VDR activation targets major pathways controlling LIC homeostasis. Induction of VDR expression and VDR signaling promoted both cell differentiation of the bulk of leukemic cells and limited LIC self-renewal. In addition, promotion of AML cell differentiation by VDR agonists eradicated LIC in mice. Together, features on induction of VDR signaling in AML cells seem to be a target for AML therapy.

Previous studies did not revealed differences in peripheral blood monocytes and myeloid differentiation induced by 12-O-tetradecanoylphorbol-13-acetate (TPA) suggesting that VDR expression is not essential for monocyte differentiation (O'Kelly et al., 2002). Our results confirmed observations that in steady-state conditions monocytes numbers are not altered in VDR−/− mice. However, HSCPs and monocyte precursors are decreased in VDR−/− suggesting that monocyte differentiation would be affected in VDR−/− mice. Thus VDR is involved in both normal and malignant hematopoiesis and found to be critical for cell stemness.

In summary, we identified here a new role of VDR and VDR signaling in normal and malignant hematopoiesis. In normal hematopoiesis VDR expression was found to be critical for HSPCS homeostasis and VDR deficient mice presented an overrepresentation of hematopoietic precursors and myeloid progenitors populations. Variations in VDR expression/function also impacted in hematopoietic malignancies since VDR/VDR-targeted gene (CAMP) expression correlated with and increased prognosis of AML patients whereas VDR inactivation in AML cells resulted in limited myeloid differentiation and increased clonogenic potential of LIC. VDR inactivation resulted from increased promoter methylation and reversal of VDR promoter hyermethylation in leukemia cells resulted in myeloid differentiation, abolition of LIC longevity and reestablishment of responsiveness to chemotherapy. Thus, VDR inactivation results in both limited myeloid differentiation and the maintenance of HSPCS longevity and induction of VDR signaling appears as an effective target pathway to eradicate LIC and therefore prevent relapses in AML therapy (FIG. 6D).

REFERENCES

Throughout this application, various references describe the state of the art to which this invention pertains. The disclosures of these references are hereby incorporated by reference into the present disclosure.

Abdel-Wahab, O., and Levine, R. L. (2013). Mutations in epigenetic modifiers in the pathogenesis and therapy of acute myeloid leukemia. Blood 121, 3563-3572.

Akalin, A., Garrett-Bakelman, F. E., Kormaksson, M., Busuttil, J., Zhang, L., Khrebtukova, I., Milne, T. A., Huang, Y., Biswas, D., Hess, J. L., et al. (2012). Base-pair resolution DNA methylation sequencing reveals profoundly divergent epigenetic landscapes in acute myeloid leukemia. PLoS Genet 8, e1002781.

Amrani, Y. M., Gill, J., Matevossian, A., Alonzo, E. S., Yang, C., Shieh, J. H., Moore, M. A., Park, C. Y., Sant'Angelo, D. B., and Denzin, L. K. (2011). The Paf oncogene is essential for hematopoietic stem cell function and development. J Exp Med 208, 1757-1765.

Bennett, J. M., Catovsky, D., Daniel, M. T., Flandrin, G., Galton, D. A., Gralnick, H. R., and Sultan, C. (1976). Proposals for the classification of the acute leukaemias. French-American-British (FAB) co-operative group. Br J Haematol 33, 451-458.

Bonnet, D., and Dick, J. E. (1997). Human acute myeloid leukemia is organized as a hierarchy that originates from a primitive hematopoietic cell. Nat Med 3, 730-737.

Callens, C., Coulon, S., Naudin, J., Radford-Weiss, I., Boissel, N., Raffoux, E., Wang, P. H., Agarwal, S., Tamouza, H., Paubelle, E., et al. (2010a). Targeting iron homeostasis induces cellular differentiation and synergizes with differentiating agents in acute myeloid leukemia. J Exp Med 207, 731-750.

Callens, C., Moura, I. C., and Hermine, O. (2010b). [Targeting oxidative metabolism to treat leukemia?]. Med Sci (Paris) 26, 1033-1035.

Castaigne, S., Pautas, C., Terre, C., Raffoux, E., Bordessoule, D., Bastie, J. N., Legrand, O., Thomas, X., Turlure, P., Reman, O., et al. (2012). Effect of gemtuzumab ozogamicin on survival of adult patients with de-novo acute myeloid leukaemia (ALFA-0701): a randomised, open-label, phase 3 study. Lancet 379, 1508-1516.

Chen, W., Kumar, A. R., Hudson, W. A., Li, Q., Wu, B., Staggs, R. A., Lund, E. A., Sam, T. N., and Kersey, J. H. (2008). Malignant transformation initiated by M11-AF9: gene dosage and critical target cells. Cancer Cell 13, 432-440.

Elstner, E., Lee, Y. Y., Hashiya, M., Pakkala, S., Binderup, L., Norman, A. W., Okamura, W. H., and Koeffler, H. P. (1994). 1 alpha,25-Dihydroxy-20-epi-vitamin D3: an extraordinarily potent inhibitor of leukemic cell growth in vitro. Blood 84, 1960-1967.

Fenaux, P. (2005). Inhibitors of DNA methylation: beyond myelodysplastic syndromes. Nat Clin Pract Oncol 2 Suppl 1, S36-44.

Fenaux, P., Mufti, G. J., Hellstrom-Lindberg, E., Santini, V., Gattermann, N., Germing, U., Sanz, G., List, A. F., Gore, S., Seymour, J. F., et al. (2010). Azacitidine prolongs overall survival compared with conventional care regimens in elderly patients with low bone marrow blast count acute myeloid leukemia. J Clin Oncol 28, 562-569.

Feng, S., Jacobsen, S. E., and Reik, W. (2010). Epigenetic reprogramming in plant and animal development. Science 330, 622-627.

Ferrara, F., and Schiffer, C. A. (2013). Acute myeloid leukaemia in adults. Lancet 381, 484-495.

Figueroa, M. E., Lugthart, S., Li, Y., Erpelinck-Verschueren, C., Deng, X., Christos, P. J., Schifano, E., Booth, J., van Putten, W., Skrabanek, L., et al. (2010). DNA methylation signatures identify biologically distinct subtypes in acute myeloid leukemia. Cancer Cell 17, 13-27.

Friedman, A. D. (2002). Transcriptional regulation of granulocyte and monocyte development. Oncogene 21, 3377-3390.

Garcia-Manero, G., and Fenaux, P. (2011). Hypomethylating agents and other novel strategies in myelodysplastic syndromes. J Clin Oncol 29, 516-523.

Ito, K., Hirao, A., Arai, F., Takubo, K., Matsuoka, S., Miyamoto, K., Ohmura, M., Naka, K., Hosokawa, K., Ikeda, Y., and Suda, T. (2006). Reactive oxygen species act through p38 MAPK to limit the lifespan of hematopoietic stem cells. Nat Med 12, 446-451.

Jung, H., Kim, M. J., Kim, D. O., Kim, W. S., Yoon, S. J., Park, Y. J., Yoon, S. R., Kim, T. D., Suh, H. W., Yun, S., et al. (2013). TXNIP Maintains the Hematopoietic Cell Pool by Switching the Function of p53 under Oxidative Stress. Cell Metab 18, 75-85.

Kim, M., Mirandola, L., Pandey, A., Nguyen, D. D., Jenkins, M. R., Turcel, M., Cobos, E., and Chiriva-Internati, M. (2012). Application of vitamin D and derivatives in hematological malignancies. Cancer Lett 319, 8-22.

Ley, T. J., Miller, C., Ding, L., Raphael, B. J., Mungall, A. J., Robertson, A., Hoadley, K., Triche, T. J. J., Laird, P. W., Baty, J. D., et al. (2013). Genomic and epigenomic landscapes of adult de novo acute myeloid leukemia. N Engl J Med 368, 2059-2074.

Lowenberg, B., Downing, J. R., and Burnett, A. (1999). Acute myeloid leukemia. N Engl J Med 341, 1051-1062.

Mardis, E. R., Ding, L., Dooling, D. J., Larson, D. E., McLellan, M. D., Chen, K., Koboldt, D. C., Fulton, R. S., Delehaunty, K. D., McGrath, S. D., et al. (2009). Recurring mutations found by sequencing an acute myeloid leukemia genome. N Engl J Med 361, 1058-1066.

Marik, R., Fackler, M., Gabrielson, E., Zeiger, M. A., Sukumar, S., Stearns, V., and Umbricht, C. B. (2010). DNA methylation-related vitamin D receptor insensitivity in breast cancer. Cancer Biol Ther 10, 44-53.

Metzeler, K. H., Hummel, M., Bloomfield, C. D., Spiekermann, K., Braess, J., Sauerland, M. C., Heinecke, A., Radmacher, M., Marcucci, G., Whitman, S. P., et al. (2008). An 86-probe-set gene-expression signature predicts survival in cytogenetically normal acute myeloid leukemia. Blood 112, 4193-4201.

Munker, R., Norman, A., and Koeffler, H. P. (1986). Vitamin D compounds. Effect on clonal proliferation and differentiation of human myeloid cells. J Clin Invest 78, 424-430.

Mupo, A., Celani, L., Dovey, O., Cooper, J. L., Grove, C., Rad, R., Sportoletti, P., Falini, B., Bradley, A., and Vassiliou, G. S. (2013). A powerful molecular synergy between mutant Nucleophosmin and Flt3-ITD drives acute myeloid leukemia in mice. Leukemia 27, 1917-1920.

Nagler, A., Riklis, I., Kletter, Y., Tatarsky, I., and Fabian, I. (1986). Effect of 1,25 dihydroxyvitamin D3 and retinoic acid on normal human pluripotent (CFU-mix), erythroid (BFU-E), and myeloid (CFU-C) progenitor cell growth and differentiation patterns. Exp Hematol 14, 60-65.

O'Kelly, J., Hisatake, J., Hisatake, Y., Bishop, J., Norman, A., and Koeffler, H. P. (2002). Normal myelopoiesis but abnormal T lymphocyte responses in vitamin D receptor knockout mice. J Clin Invest 109, 1091-1099.

Owusu-Ansah, E., and Banerjee, U. (2009). Reactive oxygen species prime Drosophila haematopoietic progenitors for differentiation. Nature 461, 537-541.

Passegue, E., Wagers, A. J., Giuriato, S., Anderson, W. C., and Weissman, I. L. (2005). Global analysis of proliferation and cell cycle gene expression in the regulation of hematopoietic stem and progenitor cell fates. J Exp Med 202, 1599-1611.

Patel, J. P., Gonen, M., Figueroa, M. E., Fernandez, H., Sun, Z., Racevskis, J., Van Vlierberghe, P., Dolgalev, I., Thomas, S., Aminova, O., et al. (2012). Prognostic relevance of integrated genetic profiling in acute myeloid leukemia. N Engl J Med 366, 1079-1089.

Paubelle, E., Zylbersztejn, F., Alkhaeir, S., Suarez, F., Callens, C., Dussiot, M., Isnard, F., Rubio, M. T., Damaj, G., Gorin, N. C., et al. (2013). Deferasirox and vitamin d improves overall survival in elderly patients with acute myeloid leukemia after demethylating agents failure. PLoS One 8, e65998.

Petrini, M., Caracciolo, F., Corini, M., Valentini, P., Sabbatini, A. R., and Grassi, B. (1991). Low-dose ARA-C and 1(OH) D3 administration in acute non lymphoid leukemia: pilot study. Haematologica 76, 200-203.

Quintas-Cardama, A., Ravandi, F., Liu-Dumlao, T., Brandt, M., Faderl, S., Pierce, S., Borthakur, G., Garcia-Manero, G., Cortes, J., and Kantarjian, H. (2012). Epigenetic therapy is associated with similar survival compared with intensive chemotherapy in older patients with newly diagnosed acute myeloid leukemia. Blood 120, 4840-4845.

Sasaki, M., Knobbe, C. B., Munger, J. C., Lind, E. F., Brenner, D., Brustle, A., Harris, I. S., Holmes, R., Wakeham, A., Haight, J., et al. (2012). IDH1(R132H) mutation increases murine haematopoietic progenitors and alters epigenetics. Nature 488, 656-659.

Sekeres, M. A., List, A. F., Cuthbertson, D., Paquette, R., Ganetzky, R., Latham, D., Paulic, K., Afable, M., Saba, H. I., Loughran, T. P., Jr., and Maciejewski, J. P. (2010). Phase I combination trial of lenalidomide and azacitidine in patients with higher-risk myelodysplastic syndromes. J Clin Oncol 28, 2253-2258.

Shearstone, J. R., Pop, R., Bock, C., Boyle, P., Meissner, A., and Socolovsky, M. (2011). Global DNA demethylation during mouse erythropoiesis in vivo. Science 334, 799-802.

Shen, L., Kantarjian, H., Guo, Y., Lin, E., Shan, J., Huang, X., Berry, D., Ahmed, S., Zhu, W., Pierce, S., et al. (2010). DNA methylation predicts survival and response to therapy in patients with myelodysplastic syndromes. J Clin Oncol 28, 605-613.

Stirewalt, D. L., Meshinchi, S., Kopecky, K. J., Fan, W., Pogosova-Agadjanyan, E. L., Engel, J. H., Cronk, M. R., Dorcy, K. S., McQuary, A. R., Hockenbery, D., et al.

(2008). Identification of genes with abnormal expression changes in acute myeloid leukemia. Genes Chromosomes Cancer 47, 8-20.

Takubo, K., Nagamatsu, G., Kobayashi, C. I., Nakamura-Ishizu, A., Kobayashi, H., Ikeda, E., Goda, N., Rahimi, Y., Johnson, R. S., Soga, T., et al. (2013). Regulation of glycolysis by Pdk functions as a metabolic checkpoint for cell cycle quiescence in hematopoietic stem cells. Cell Stem Cell 12, 49-61.

Terpstra, W., Ploemacher, R. E., Prins, A., van Lom, K., Pouwels, K., Wognum, A. W., Wagemaker, G., Lowenberg, B., and Wielenga, J. J. (1996). Fluorouracil selectively spares acute myeloid leukemia cells with long-term growth abilities in immunodeficient mice and in culture. Blood 88, 1944-1950.

Tothova, Z., Kollipara, R., Huntly, B. J., Lee, B. H., Castrillon, D. H., Cullen, D. E., McDowell, E. P., Lazo-Kallanian, S., Williams, I. R., Sears, C., et al. (2007). FoxOs are critical mediators of hematopoietic stem cell resistance to physiologic oxidative stress. Cell 128, 325-339.

Walter, R. B., Othus, M., Burnett, A. K., Lowenberg, B., Kantarjian, H. M., Ossenkoppele, G. J., Hills, R. K., van Montfort, K. G., Ravandi, F., Evans, A., et al. (2013). Significance of FAB subclassification of "acute myeloid leukemia, NOS" in the 2008 WHO classification: analysis of 5848 newly diagnosed patients. Blood 121, 2424-2431.

Welch, J. S., Ley, T. J., Link, D. C., Miller, C. A., Larson, D. E., Koboldt, D. C., Wartman, L. D., Lamprecht, T. L., Liu, F., Xia, J., et al. (2012). The origin and evolution of mutations in acute myeloid leukemia. Cell 150, 264-278.

The invention claimed is:

1. A method of restoring or enhancing sensitivity to a chemotherapeutic agent in a patient suffering from hematopoietic malignancy, comprising simultaneously or sequentially administering to the patient a combination of:
   i. a DNA methylation inhibitor; and
   ii. inecalcitol in an amount sufficient to restore or enhance sensitivity to the chemotherapeutic agent,
   wherein said hematopoietic malignancy is acute myeloid leukemia,
   wherein said acute myeloid leukemia is AML with normal karyotype with mutations in a gene selected from the group consisting of: FLT3, NPM1, KIT, CEBPA and MLL,
   wherein said acute myeloid leukemia expresses mutated FLT3-ITD.

2. The method according to claim 1, wherein said DNA methylation inhibitor is azacytidin.

3. A method for treating a drug resistant cancer and/or for preventing a tumor relapse in a patient suffering from hematopoietic malignancy, comprising the step of simultaneously or sequentially administering to the patient a combination of:
   i. a DNA methylation inhibitor; and
   ii. inecalcitol,
in an amount sufficient to treat the drug resistant cancer and/or to prevent tumor relapse in the patient,
   wherein said hematopoietic malignancy is selected from the group consisting of acute myeloid leukemia,
   wherein the acute myeloid leukemia is AML with normal karyotype with mutations in a gene selected from the group consisting of: FLT3, NPM1, KIT, CEBPA and MLL,
   wherein said acute myeloid leukemia expresses mutated FLT3-ITD.

4. The method according to claim 3, wherein said DNA methylation inhibitor is azacytidin.

* * * * *